United States Patent
Herget et al.

(10) Patent No.: US 12,352,714 B2
(45) Date of Patent: Jul. 8, 2025

(54) DEVICES, SYSTEMS AND METHODS TO DETECT THE PRESENCE OF ß-LACTAM ANTIBIOTIC HYDROLYZING BACTERIA IN A SAMPLE

(71) Applicant: Avalis Medical, Inc., Menlo Park, CA (US)

(72) Inventors: Meike Herget, Woodside, CA (US); Oren S. Knopfmacher, San Francisco, CA (US); Michael D. Laufer, Menlo Park, CA (US)

(73) Assignee: Avails Medical, Inc., Menlo Park, CA (US)

( * ) Notice: Subject to any disclaimer, the term of this patent is extended or adjusted under 35 U.S.C. 154(b) by 441 days.

(21) Appl. No.: 16/440,829

(22) Filed: Jun. 13, 2019

(65) Prior Publication Data
US 2019/0310214 A1    Oct. 10, 2019

Related U.S. Application Data

(63) Continuation of application No. PCT/US2016/066315, filed on Dec. 13, 2016.

(51) Int. Cl.
*G01N 27/02* (2006.01)
*C12N 1/06* (2006.01)
(Continued)

(52) U.S. Cl.
CPC .............. *G01N 27/021* (2013.01); *C12N 1/06* (2013.01); *C12Q 1/18* (2013.01); *C12Q 1/34* (2013.01)

(58) Field of Classification Search
CPC .......... G01N 27/021; C12Q 1/18; C12N 1/18; C12N 1/34; C12N 1/06
(Continued)

(56) References Cited

U.S. PATENT DOCUMENTS

| | | |
|---|---|---|
| 3,743,581 A | 7/1973 | Cady et al. |
| 4,200,493 A | 4/1980 | Wilkins et al. |

(Continued)

FOREIGN PATENT DOCUMENTS

| | | |
|---|---|---|
| EP | 0235024 | 9/1987 |
| EP | 1460130 | 9/2004 |

(Continued)

OTHER PUBLICATIONS

Berney et al. "A DNA diagnostic biosensor: development, characterization and performance" Sensors and Actuators B: Chemical: International Journal Devoted to Research and Development of Physical and Chemical Transducers, Elsevier BV, NL, vol. 68, No. 1-3, Aug. 25, 2000, pp. 100-108.

(Continued)

*Primary Examiner* — Jennifer M. H. Tichy
(74) *Attorney, Agent, or Firm* — Levine Bagade Han LLP

(57) ABSTRACT

Various devices, systems and methods for detecting the presence of β-lactam antibiotic hydrolyzing bacteria in a sample are disclosed. In one embodiment, a method of detecting the presence of β-lactam antibiotic hydrolyzing bacteria includes introducing the sample to a filter configured to capture bacteria in the sample; introducing a buffer solution to the bacteria captured on the filter surface, wherein the buffer solution comprises a β-lactamase substrate, a β-lactamase activator, and a lysing agent to lyse cells of the bacteria to release β-lactam antibiotic hydrolyzing enzymes; exposing a sensor having an electrical characteristic to a reaction mixture comprising the buffer solution and the β-lactam antibiotic hydrolyzing enzymes; and monitoring a change in the electrical characteristic of the sensor to detect the presence of the β-lactam antibiotic hydrolyzing bacteria in the sample originally introduced.

13 Claims, 15 Drawing Sheets

(51) Int. Cl.
  *C12Q 1/18* (2006.01)
  *C12Q 1/34* (2006.01)
(58) Field of Classification Search
  USPC .......................................................... 435/18
  See application file for complete search history.

(56) References Cited

U.S. PATENT DOCUMENTS

| | | |
|---|---|---|
| 4,236,893 A | 12/1980 | Rice |
| 4,314,821 A | 2/1982 | Rice |
| 4,448,534 A | 5/1984 | Wertz et al. |
| 4,735,906 A | 4/1988 | Bastiaans |
| 4,767,719 A | 8/1988 | Finlan |
| 4,789,804 A | 12/1988 | Karube et al. |
| 4,822,566 A | 4/1989 | Newman |
| 4,965,193 A | 10/1990 | Chen |
| 4,977,247 A | 12/1990 | Fahnestock et al. |
| 5,064,756 A | 11/1991 | Carr et al. |
| 5,077,210 A | 12/1991 | Eigler et al. |
| 5,111,221 A | 5/1992 | Fare et al. |
| 5,172,332 A | 12/1992 | Hungerford et al. |
| 5,182,005 A | 1/1993 | Schwiegk et al. |
| 5,447,845 A | 9/1995 | Chu et al. |
| 5,821,399 A | 10/1998 | Zelin |
| 5,922,537 A | 7/1999 | Ewart et al. |
| 6,280,586 B1 | 8/2001 | Wolf et al. |
| 6,368,795 B1 | 4/2002 | Hefti |
| 6,391,558 B1 | 5/2002 | Henkens et al. |
| 6,391,577 B1 | 5/2002 | Mikkelsen et al. |
| 6,548,263 B1 | 4/2003 | Kapur et al. |
| 6,548,311 B1 | 4/2003 | Knoll |
| 6,780,307 B2 | 8/2004 | Kidwell |
| 6,863,792 B1 | 3/2005 | Madou et al. |
| 7,745,272 B2 | 6/2010 | Van De Walle et al. |
| 8,508,100 B2 | 8/2013 | Lee et al. |
| 8,728,844 B1 | 5/2014 | Liu et al. |
| 9,377,456 B1 | 6/2016 | Herget et al. |
| 9,702,847 B2 | 7/2017 | Herget et al. |
| 9,766,201 B2 | 9/2017 | Herget et al. |
| 9,944,969 B2 | 4/2018 | Knopfmacher et al. |
| 9,963,733 B2 | 5/2018 | Knopfmacher et al. |
| 10,060,916 B2 | 8/2018 | Knopfmacher |
| 10,174,356 B2 | 1/2019 | Knopfmacher et al. |
| 10,254,245 B2 | 4/2019 | Knopfmacher et al. |
| 2002/0127623 A1 | 9/2002 | Minshull et al. |
| 2003/0073071 A1 | 4/2003 | Fritz et al. |
| 2003/0109056 A1 | 6/2003 | Vossmeyer et al. |
| 2003/0119208 A1 | 6/2003 | Yoon et al. |
| 2004/0195098 A1 | 10/2004 | Broadley et al. |
| 2006/0102935 A1 | 5/2006 | Yitzchaik et al. |
| 2006/0197118 A1 | 9/2006 | Migliorato et al. |
| 2006/0246426 A1 | 11/2006 | Woodbury et al. |
| 2006/0286548 A1 | 12/2006 | Liposky |
| 2007/0037225 A1 | 2/2007 | Metzger et al. |
| 2007/0054396 A1 | 3/2007 | Peppers et al. |
| 2007/0072187 A1 | 3/2007 | Blok et al. |
| 2008/0012007 A1 | 1/2008 | Li et al. |
| 2008/0199863 A1 | 8/2008 | Haake et al. |
| 2009/0008247 A1 | 1/2009 | Chen et al. |
| 2009/0020438 A1 | 1/2009 | Hodges |
| 2009/0273354 A1 | 11/2009 | Dhirani et al. |
| 2010/0025660 A1 | 2/2010 | Jain et al. |
| 2010/0137143 A1 | 6/2010 | Rothberg et al. |
| 2010/0194409 A1 | 8/2010 | Gao et al. |
| 2011/0068372 A1 | 3/2011 | Ren et al. |
| 2011/0306032 A1 | 12/2011 | Galiano et al. |
| 2012/0032235 A1 | 2/2012 | Bikumandla |
| 2012/0077692 A1 | 3/2012 | Hassibi et al. |
| 2012/0088682 A1 | 4/2012 | Rothberg et al. |
| 2012/0143027 A1 | 6/2012 | Phillips et al. |
| 2012/0153262 A1 | 6/2012 | Paranjape et al. |
| 2012/0153407 A1 | 6/2012 | Chang et al. |
| 2012/0165246 A1 | 6/2012 | Lindner et al. |
| 2012/0168306 A1 | 7/2012 | Hassibi et al. |
| 2012/0208291 A1 | 8/2012 | Davis et al. |
| 2012/0261274 A1 | 10/2012 | Rearick et al. |
| 2012/0256166 A1 | 11/2012 | Chen et al. |
| 2012/0279859 A1 | 11/2012 | Rothberg et al. |
| 2013/0089883 A1 | 4/2013 | Dallenne et al. |
| 2013/0089932 A1 | 4/2013 | Wu et al. |
| 2013/0096013 A1 | 4/2013 | Esfandyarpour et al. |
| 2013/0105868 A1 | 5/2013 | Kalnitsky et al. |
| 2013/0217063 A1 | 8/2013 | Metzger et al. |
| 2014/0011218 A1 | 1/2014 | Han et al. |
| 2014/0057339 A1 | 2/2014 | Esfandyarpour et al. |
| 2014/0134656 A1 | 5/2014 | Dortet et al. |
| 2014/0191294 A1 | 7/2014 | Bikumandla et al. |
| 2014/0231256 A1 | 8/2014 | Packingham et al. |
| 2014/0349005 A1 | 11/2014 | Everett et al. |
| 2015/0355129 A1 | 12/2015 | Knopfmacher |
| 2016/0039657 A1 | 2/2016 | Jain et al. |
| 2016/0068417 A1 | 3/2016 | Buschmann |
| 2016/0160268 A1* | 6/2016 | Haake .................... C12Q 1/689 |
| | | 506/9 |
| 2016/0187332 A1 | 6/2016 | Herget et al. |
| 2016/0187334 A1 | 6/2016 | Herget et al. |
| 2016/0208306 A1 | 7/2016 | Pollak et al. |
| 2016/0209356 A1 | 7/2016 | Herget et al. |
| 2016/0266102 A1 | 9/2016 | Knopfmacher |
| 2017/0058313 A1 | 3/2017 | Knopfmacher et al. |
| 2017/0059508 A1 | 3/2017 | Knopfmacher et al. |
| 2017/0212075 A1 | 7/2017 | Knopfmacher et al. |
| 2017/0336348 A1 | 11/2017 | Herget et al. |
| 2017/0342459 A1 | 11/2017 | Knopfmacher et al. |
| 2018/0195106 A1 | 7/2018 | Knopfmacher et al. |
| 2018/0364221 A1 | 12/2018 | Knopfmacher |
| 2019/0046984 A1 | 2/2019 | Kelley et al. |
| 2019/0136290 A1 | 5/2019 | Knopfmacher et al. |
| 2019/0293529 A1 | 9/2019 | Rajan et al. |
| 2020/0150082 A1 | 5/2020 | Knopfmacher et al. |

FOREIGN PATENT DOCUMENTS

| | | |
|---|---|---|
| JP | 1988-066454 | 3/1988 |
| JP | 1996-0886771 | 4/1996 |
| JP | 2006-511818 | 4/2006 |
| JP | 2011-58900 | 3/2011 |
| JP | 2011-085038 | 11/2012 |
| WO | WO 2003/044530 | 5/2003 |
| WO | WO 2003/052097 | 6/2003 |
| WO | WO 2004/077052 | 9/2004 |
| WO | WO 2006/102695 | 10/2006 |
| WO | WO 2007/035814 | 3/2007 |
| WO | WO 2010/062001 | 6/2010 |
| WO | WO 2012/078340 | 6/2012 |
| WO | WO 2013/096404 | 6/2013 |
| WO | WO 2014/080292 | 5/2014 |
| WO | WO 2014/134431 | 9/2014 |
| WO | WO 2015/077632 | 5/2015 |
| WO | WO 2015/188002 | 12/2015 |
| WO | WO 2016/005743 | 1/2016 |
| WO | WO 2016/028233 | 2/2016 |
| WO | WO 2016/044417 | 3/2016 |
| WO | WO 2016/061453 | 4/2016 |
| WO | WO 2016/109569 | 7/2016 |
| WO | WO 2017/035393 | 3/2017 |
| WO | WO 2017/107333 | 6/2017 |
| WO | WO 2017/132095 | 8/2017 |
| WO | WO 2017/209839 | 12/2017 |
| WO | WO 2018/111234 | 6/2018 |
| WO | WO 2018/145338 | 8/2018 |
| WO | WO 2019/005296 | 1/2019 |
| WO | WO 2019/070739 | 4/2019 |
| WO | WO 2019/113226 | 6/2019 |
| WO | WO 2019/246208 | 12/2019 |

OTHER PUBLICATIONS

Dortet, Laurent et al., "Bloodstream Infections Caused by *Pseudomonas* spp.: How to Detect Carbapenemase Producers Directly from Blood Cultures", Journal of Clinical Microbiology, 52(4):1269-1273, Apr. 2014.

(56) References Cited

OTHER PUBLICATIONS

Dortet, Laurent et al., "CarbAcineto NP Test for Rapid Detection of Carbapenemase-Producing *Acinetobacter* spp.", Journal of Clinical Microbiology, 52(7):2359-2364, Jul. 2014.

Dortet, Laurent et al., "Evaluation of the RapidECw Carba NP, the Rapid CARB Screenw and the Carba NP test for biochemical detection of carbapenemase-producing Enterobacteriaceae", J Antimicrob Chemother, 70:3014-3022, 2015.

Dortet, Laurent et al., "Further Proofs of Concept for the Carba NP Test", Antimicrobial Agents and Chemotherapy, 58(2):1269, Feb. 2014.

Dortet, Laurent et al., "Rapid Identification of Carbapenemase Types in Enterobacteriaceae and *Pseudomonas* spp. by Using a Biochemical Test", Antimicrobial Agents and Chemotherapy, 56(12):6437-6440, Dec. 2012.

Estrela, Pedro et al., "Label-Free Sub-picomolar Protein Detection with Field-Effect Transistors," Analytical Chemistry, vol. 82, No. 9, May 1, 2010, 3531-3536.

Hammock, Mallory L. et al., "Electronic readout ELISA with organic field-effect transistors as a prognostic test for preeclampsia," Advanced Materials, 26: 6138-6144. doi: 10.1002/adma. 201401829.

Kumar et al., "Sensitivity Enhancement Mechanisms in Textured Dielectric Based Electrolyte-Insulator-Semiconductor (EIS) Sensors," *ECS Journal of Solid State Science and Technology*, 4(3):N18-N23 (2015).

Mathias, W. et al., "Selective Sodium Sensing with Gold-Coated Silicon Nanowire Field-Effect Transistors in a Differential Setup," ACS Nano 7, 5978-5983 (2013).

Nordmann, Patrice et al., "Strategies for identification of carbapenemase-producing Enterobacteriaceae", J Antimicrob Chemother, 68:487-489, 2013.

Oliu et al., "Impedimetric Sensors for Bacteria Detection," Biosensors—Micro and Nanoscale Applications, Chpt. 9 (Sep. 2015) p. 257-288.

Poghossian et al., "Penicillin Detection by Means of Field-Effect Based Sensors: EnFET, Capacitive EIS Sensor or LAPS?", *Sensors and Actuators B*, 78:237 (2001).

Poirel, Laurent et al., "Rapidec Carba NP Test for Rapid Detection of Carbapenemase Producers", Journal of Clinical Microbiology, 53(9):3003-3008, Sep. 2015.

Pourciel-Gouzy M L et al: "pH-ChemFET-based analysis devices for the bacterial activity monitoring." Sensors and Actuators B: Chemical: International Journal Devoted to Research and Development of Physical and Chemical Transducers, Elsevier BV, NL, vol. 134, No. Aug. 1, 28, 2008, pp. 339-344.

Salm, Eric et al., "Electrical Detection of Nucleic Acid Amplification Using an On-Chip Quasi-Reference Electrode and a PVC REFET," dx.doi.org/10.1021/ac500897t, *Anal. Chem.*, 2014, 86, 6968-6975.

Schoning, Michael J., "'Playing Around' with Field-Effect Sensors on the Basis of EIS Structures, LAPS and ISFETs," Sensors, 5:126-138 (2005).

Grossi Marco et al. "Bacterial concentration detection using a portable embedded sensor system for environmental monitoring", 2017 7th IEE International Workshop on Advances in Senors and Interfaces (IWASI), IEEE, Jun. 15, 2017, pp. 246-251.

Ivnitsky D et al: "Biosensors for Detection of Pathogenic Bacteria", Biosensors and Bioelectronics, Elsevier Science Ltd. UK, Amsterdam, NL, vol. 14, No. 7, Oct. 1, 1999, pp. 599-624.

J. Parce et al: "Detection of cell-affecting agents with a silicon biosensor", Science, vol. 246, No. 4927, Oct. 13, 1989 (Oct. 13, 1989), pp. 243-247.

Yu Allen C et al: Moni tori ng bacterial growth using tunable resistive pulse sensing with a pore-based technique11 , Applied Microbiology and Biotechnology, Springer Berlin Heidelberg, Berlin/Heidelberg, vol. 98, No. 2, Nov. 29, 2013, pp. 855-862.

Zhang, Xuzhi et al.: Online Monitoring of Bacterial Growth with an Electrical Sensor11 Analytical Chemistry, vol. 90, No. 10, Apr. 24, 2018 (Apr. 24, 2018), pp. 6006-6011.

Zhou, Yong-Jun et al.: Real-time Detection System for Amount of Bacteria Based on an Electrochemical Sensor, Instrument Technique and Sensor, vol. 2, No. 2, Feb. 28, 2014 (Feb. 28, 2014), pp. 71-72 and 86.

Dutton 1978 (Redox potentiometry: Determination of midpoint potentials of oxidation-reduction components of biological electron-transfer systems; In Methods in Enzymology, 54:411-435) (Year: 1978).

Wan et al., 2011 (Impedimetric immunosensor doped with reduced graphene sheets fabricated by controllable electrodeposition for the non-labelled detection of bacteria; Biosensors and Bioelectronics 26 (2011) 1959-1964). (Year: 2011).

Zuhri et al. 2016 (Effect of Methylene Blue Addition as a Redox Mediator on Performance of Microbial Desalination Cell by Utilizing Tempe Wastewater; International Journal ofTechnology 6: 952-961). (Year: 2016).

Kang et al. "Survey of Redox-Active Moieties for Application in Multiplexed Electrochemical Biosensors", Anal. Chem., vol. 88, pp. 10452-10458, 2016.

Torriero, Angel AJ, "Understanding the Differences between a Quasi-Reference Electrode and a Reference Electrode", Medicinal & Analytical Chemistry International Journal, vol. 3, Issue 3, Aug. 26, 2019, p. 1-3.

* cited by examiner

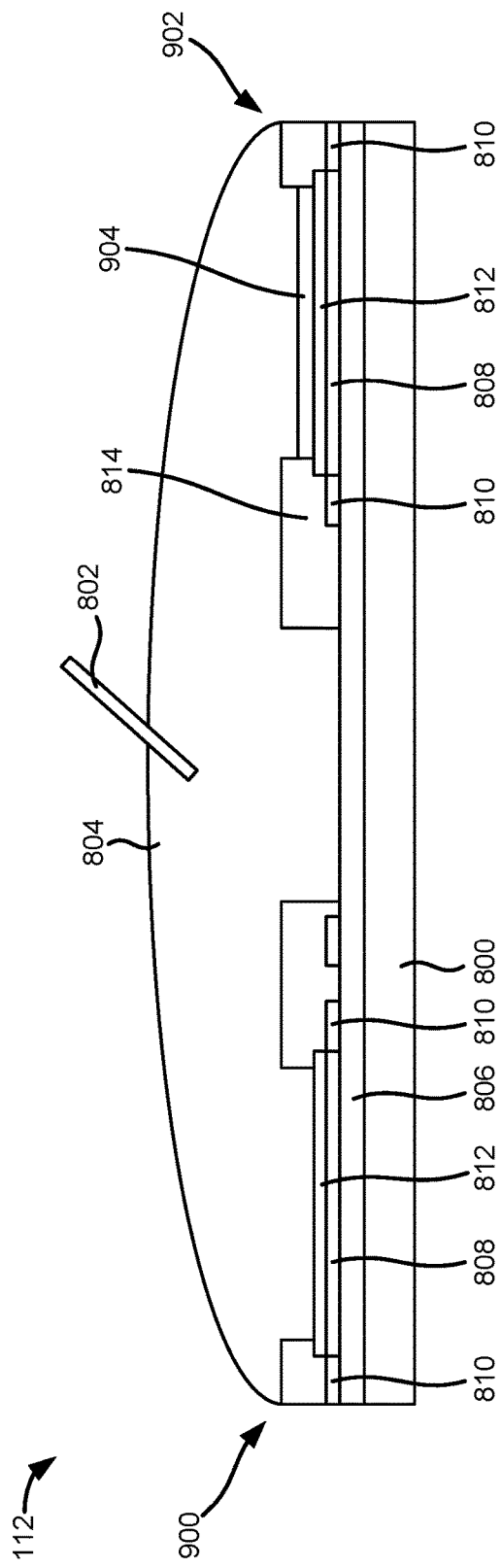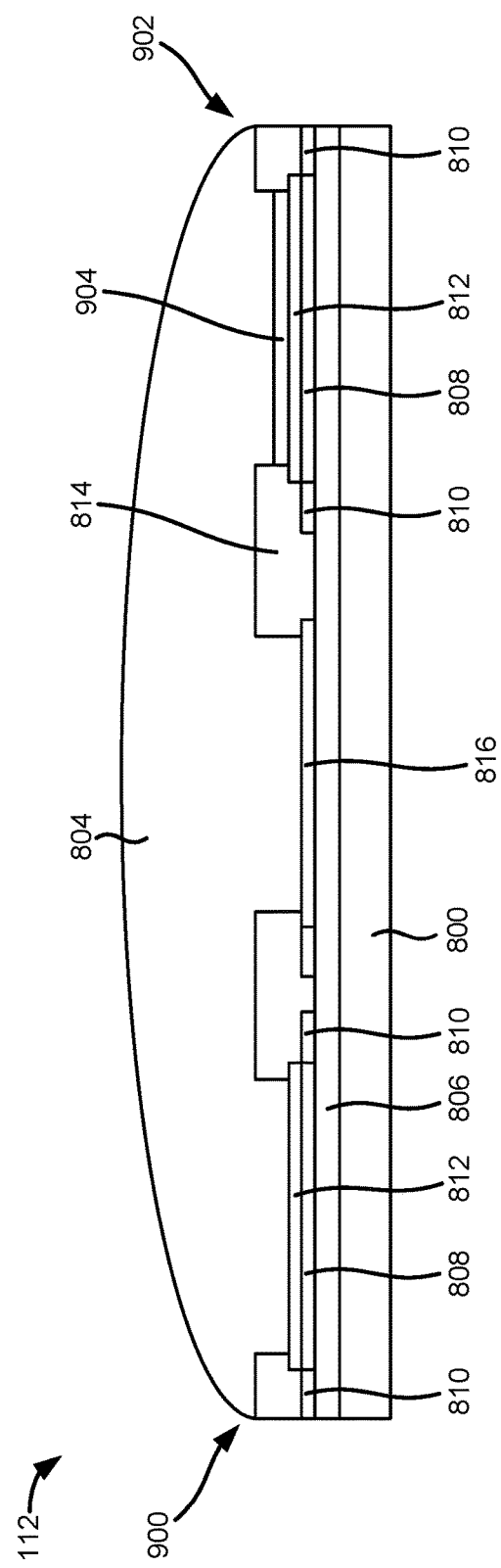

DEVICES, SYSTEMS AND METHODS TO DETECT THE PRESENCE OF ß-LACTAM ANTIBIOTIC HYDROLYZING BACTERIA IN A SAMPLE

CROSS-REFERENCE TO RELATED APPLICATION

This application is a continuation of PCT Application No. PCT/US2016/066315 filed on Dec. 13, 2016, the content of which is hereby incorporated by reference in its entirety.

TECHNICAL FIELD

The present disclosure relates generally to the detection of β-lactam antibiotic hydrolyzing bacteria. More specifically, the present disclosure relates to devices, systems, and methods to detect the presence of β-lactam antibiotic hydrolyzing bacteria in a sample.

BACKGROUND

Antibiotic resistant bacteria that express β-lactamase enzymes, including extended spectrum β-lactamases (ESBLs) and carbapenemases, are a significant problem for healthcare professionals in hospitals, nursing homes, and other healthcare environments. Rapid detection of such bacteria is crucial in order to prevent the spread of their antibiotic resistance capabilities to other bacteria though horizontal gene transfer.

Existing methods for detecting β-lactam antibiotic hydrolyzing bacteria require the use of costly and labor intensive microbial culturing techniques to isolate the β-lactam antibiotic hydrolyzing bacteria. In addition, devices for detecting the presence of β-lactam antibiotic hydrolyzing bacteria often rely on an optical read-out of the investigated samples which must be monitored continuously over a period of hours by skilled personnel. Such devices or techniques are prone to clinician error, require lengthy sample preparation times, and don't allow for high throughput or automated analysis of several samples at a time.

As a result of the above limitations and restrictions, there is a need for improved devices, systems, and methods to quickly and effectively detect the presence of β-lactam antibiotic hydrolyzing bacteria and to detect such bacteria using a clinical sample without further culturing. Moreover, such a solution should be able to accommodate high-throughput detection and provide an electronic read-out that can be captured and recorded for epidemiological purposes.

SUMMARY

Various devices, systems and methods for detecting the presence of β-lactam antibiotic hydrolyzing bacteria in sample are described herein. In one embodiment, a method of detecting the presence of β-lactam antibiotic hydrolyzing bacteria in a sample is disclosed. The method includes introducing the sample to a filter comprising a filter surface. The filter surface can be configured to capture bacteria in the sample. The method can also include introducing a buffer solution to the bacteria captured on the filter surface. The buffer solution can comprise a β-lactamase substrate, a β-lactamase activator and inhibitor, and a lysing agent to lyse cells of the bacteria to release β-lactam antibiotic hydrolyzing enzymes. The buffer solution and the β-lactam antibiotic hydrolyzing enzymes can form a reaction mixture. The method can further include exposing a sensor having an electrical characteristic to the reaction mixture and monitoring a change in the electrical characteristic of the sensor to detect the presence of the β-lactam antibiotic hydrolyzing bacteria in the sample originally introduced.

In another embodiment, a method of detecting the presence of β-lactam antibiotic hydrolyzing bacteria in a sample is disclosed. The method can also include delivering a reaction buffer to the bacteria captured on the filter surface. The reaction buffer can comprise a β-lactamase activator and a lysing agent to lyse cells of the bacteria to release β-lactam antibiotic hydrolyzing enzymes. The reaction buffer and the β-lactam antibiotic hydrolyzing enzymes can form a reaction effluent. The method can also include delivering, using a multichannel delivery device, the reaction effluent to a well plate comprising a plurality of reaction wells. Each of the plurality of reaction wells can comprise a β-lactamase substrate and the reaction effluent and the β-lactamase substrate can form a reaction mixture. The method can further include exposing a sensor having an electrical characteristic to the reaction mixture in at least one of the plurality of reaction wells and monitoring a change in the electrical characteristic of the sensor to detect the presence of the β-lactam antibiotic hydrolyzing bacteria in the sample originally introduced.

In another embodiment, a system to detect the presence of β-lactam antibiotic hydrolyzing bacteria in a sample is disclosed. The system can include a filter comprising a filter surface. The filter surface can be configured to receive the sample and capture bacteria in the sample. The system can also include a fluid delivery conduit configured to deliver a reaction buffer to the bacteria captured on the filter surface. The reaction buffer can comprise a β-lactamase activator and a lysing agent to lyse cells of the bacteria to release β-lactam antibiotic hydrolyzing enzymes. The reaction buffer and the β-lactam antibiotic hydrolyzing enzymes can form a reaction effluent. The system can further include a well plate comprising a plurality of reaction wells. Each of the plurality of reaction wells can comprise at least one β-lactamase substrate. The system can also include a multichannel delivery device configured to deliver the reaction effluent to the well plate. The reaction effluent and the β-lactamase substrate can form a reaction mixture. The system can also include a pH sensor configured to measure the pH of the reaction mixture in at least one of the plurality of reaction wells. A decrease in the pH of the reaction well measured can indicate the presence of β-lactam antibiotic hydrolyzing bacteria in the sample originally introduced.

In yet another embodiment, a method of detecting the presence of β-lactam antibiotic hydrolyzing bacteria in a sample is disclosed. The method can include introducing the sample to a filter comprising a filter surface, wherein the filter surface is configured to capture bacteria in the sample and at least some of the bacteria secrete β-lactam antibiotic hydrolyzing enzymes. The method can also include introducing a buffer solution to the bacteria captured on the filter surface, wherein the buffer solution comprises a β-lactamase substrate and a β-lactamase activator. The buffer solution and the β-lactam antibiotic hydrolyzing enzymes secreted by the bacteria can form a reaction mixture. The method can further include exposing a sensor having an electrical characteristic to the reaction mixture and monitoring a change in the electrical characteristic of the sensor to detect the presence of the β-lactam antibiotic hydrolyzing bacteria in the sample originally introduced.

BRIEF DESCRIPTION OF THE SEVERAL VIEWS OF THE DRAWINGS

FIG. 9A illustrates a side view of another embodiment of a sensor of the system having an active sensor, a control sensor, and an external reference electrode.

FIG. 9B illustrates a side view of another embodiment of a sensor of the system having an active sensor, a control sensor, and an on-chip reference electrode.

DETAILED DESCRIPTION

Variations of the devices, systems, and methods described herein are best understood from the detailed description when read in conjunction with the accompanying drawings. It is emphasized that, according to common practice, the various features of the drawings may not be to scale. On the contrary, the dimensions of the various features may be arbitrarily expanded or reduced for clarity and not all features may be visible or labeled in every drawing. The drawings are taken for illustrative purposes only and are not intended to define or limit the scope of the claims to that which is shown.

Figure 1A:
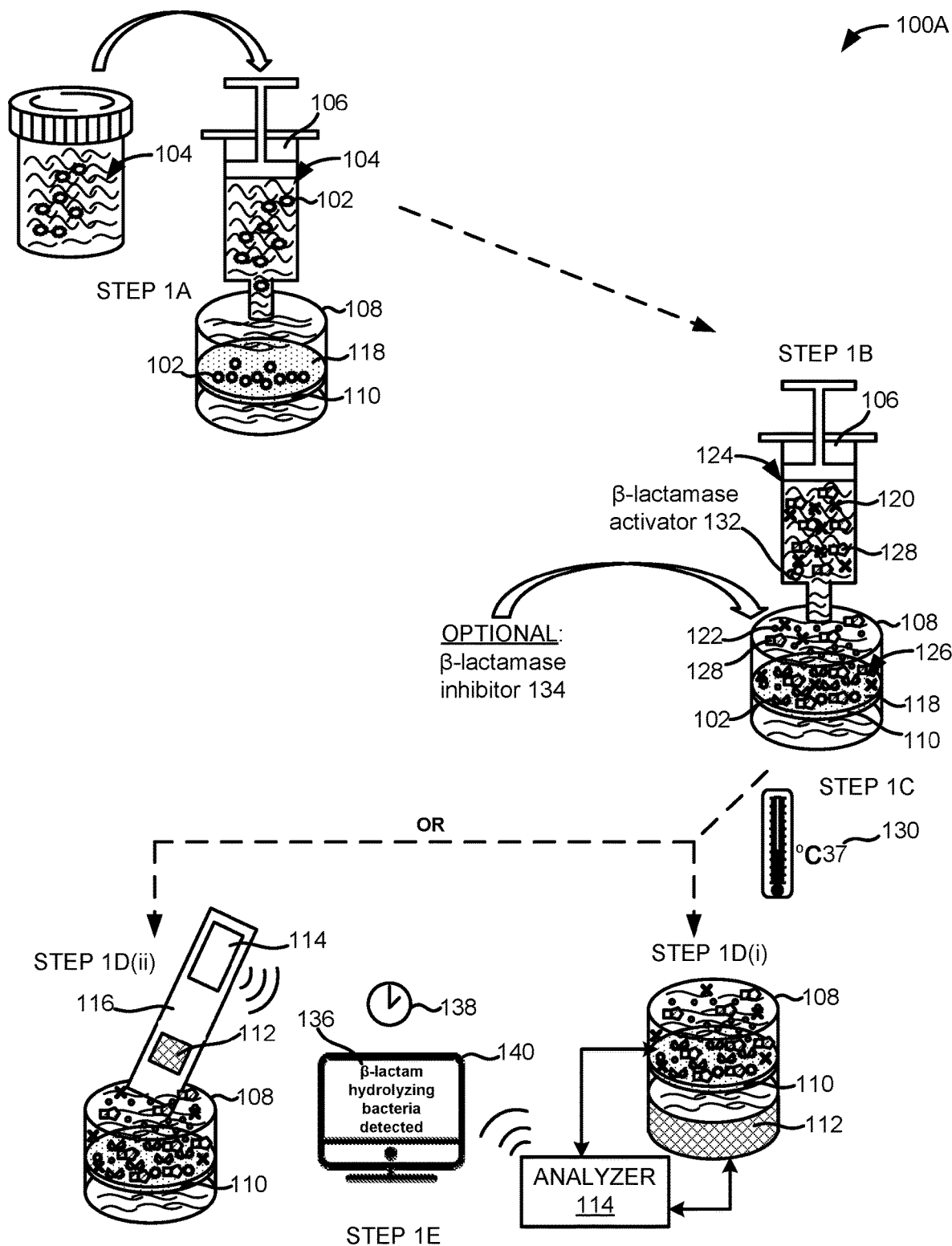
FIG. 1A illustrates one embodiment of a system and a method of operation thereof for detecting β-lactam antibiotic hydrolyzing bacteria in a sample.

FIG. 1A illustrates an embodiment of a system 100A for detecting β-lactam antibiotic hydrolyzing bacteria 136 in a sample 104. In one embodiment, the system 100A can comprise a fluid delivery conduit 106, a filter housing 108 containing a filter 110, a sensor 112, and a parameter analyzer 114. The sensor 112 can be located on a substrate 116.

The substrate 116 can be comprised of a polymer or polymeric material, a metal, a ceramic, a semiconductor layer, an oxide layer, an insulator, or a combination thereof. As shown in FIG. 1A, the parameter analyzer 114 can be integrated into one device with the sensor 112. For example, the parameter analyzer 114 can be fabricated on the same substrate 116 as the sensor 112. In other embodiments, the parameter analyzer 114 can be a standalone unit or device coupled to the sensor 112. The sensor 112 will be discussed in more detail in the sections that follow.

The sample 104 can comprise at least one of a biological sample, a bodily fluid, and a bacterial culture derived from the biological sample or the bodily fluid. The bodily fluid can comprise urine, blood, serum, plasma, saliva, sputum, semen, breast milk, joint fluid, spinal fluid, wound material, mucus, fluid accompanying stool, re-suspended rectal or wound swabs, or a combination thereof. In other embodiments, the sample 104 can also comprise an environmental fluid such as liquids sampled from a stream, river, lake, ocean, contamination site, quarantine zone, or emergency area. The sample 104 can also be a food sample.

The sample 104 can carry or contain bacteria 102. The bacteria 102 can include gram negative bacteria, gram positive bacteria, or a combination thereof. The bacteria 102 can also include antibiotic resistant bacteria, antibiotic susceptible or intermediate resistant bacteria, or a combination thereof. For example, the bacteria 102 can include β-lactam antibiotic hydrolyzing bacteria 136.

The fluid delivery conduit 106 can be a tube or channel for delivering buffers, reagents, fluid samples including the sample 104 to devices, apparatus, or containers in the system. For example, as shown in FIG. 1A, the fluid delivery conduit 106 can be or refer to part of a pump such as a syringe pump. In other embodiments, the fluid delivery conduit 106 can include or refer to at least part of a hydraulic pump, a pneumatic pump, a peristaltic pump, a vacuum pump, or a combination thereof. In additional embodiments, the fluid delivery conduit 106 can include or refer to at least part of an injection cartridge, a microfluidic channel, a pipette, a reaction tube, a capillary, a test tube, or a combination thereof. The fluid delivery conduit 106 can be part of a vacuum system configured to draw fluid to or through the filter 110 under vacuum. Moreover, the fluid delivery conduit 106 can include or refer to at least part of a multichannel delivery device or pipette.

The filter housing 108 can be a container or vessel configured to secure or enclose the filter 110. For example, the filter housing 108 can be a protective chamber. The protective chamber can be an electrically isolated environment. The protective chamber can also be a temperature controlled chamber, a light controlled chamber, or a combination thereof.

The filter 110 can have a filter surface 118. The filter 110 can trap or isolate the bacteria 102 by depositing or capturing the bacteria 102 on to the filter surface 118. The filter surface 118 can be an external surface, an internal surface extending into the filter 110, or a combination thereof. The filter 110 can be made of, but is not limited to, cellulose acetate, regenerated cellulose, nylon, polystyrene, polyvinylidene fluoride (PVDF), polyethersulfone (PES), polytetrafluoroethylene (PTFE), glass microfiber, or a combination thereof.

In one embodiment, the filter 110 can have filter pores of sequentially smaller pore size. For example, the filter 110 can have larger filter pores at the top of the filter and progressively smaller filters pores toward the bottom of the filter. In another embodiment, the filter 110 can have filter pores of a similar pore size throughout the entire filter. In these embodiments, the filter surface 118 can be the surface of the pores. In another embodiment, the filter 110 can be a mesh or matrix structure and the filter surface 118 can be a mesh or matrix surface.

The filter 110 can be a non-clogging filter such as a high-capacity filter. Although not shown in FIG. 1A, it is contemplated by this disclosure that the filter 110 can refer to a plurality of filters in a stacked arrangement.

The filter 110 can capture and hold the bacteria 102 when a sample 104 comprising or carrying the bacteria 102 is introduced to the filter 110 in step 1A shown in FIG. 1A. For example, the sample 104 can be introduced to the filter 110 when the sample 104 is poured over the filter 110 or injected through the filter 110. The filter 110 can isolate or separate the bacteria 102 or other molecules or cells from the supernatant of the sample 104.

In one embodiment, the filter housing 108 can have at least one opening which allows fluid or supernatant from the sample 104 to evacuate the filter housing 108. For example, step 1A can include the additional step of discarding the fluid or supernatant from the sample 104 through the opening after isolating the bacteria 102 on the filter surface 118. Although the filter housing 108 is shown as a separate container or apparatus from the fluid delivery conduit 106, it is contemplated by this disclosure that the filter housing 108 and the filter 110 can be integrated with the fluid delivery conduit 106 or serve as an attachment to the fluid delivery conduit 106. For example, the filter housing 108 can be a part of a syringe serving as the fluid delivery conduit 106. In another example, the filter housing 108 can be a syringe filter and the filter surface 118 can be a filter surface within the syringe filter.

In an alternative embodiment not shown in FIG. 1A, a stimulus solution can be added to the sample 104 before introducing the sample 104 to the filter 110. The stimulus solution can be a nutrient or growth solution. The stimulus solution can be a super nutrient solution.

The sample 104 can also be pre-filtered in a step before step 1A. This pre-filtering step can involve filtering the sample 104 using an additional filter, a microfluidic filter, or a combination thereof to filter out other larger cellular components including blood cells or epithelial cells from the sample 104 when the sample 104 is composed of bodily fluid.

The same fluid delivery conduit 106 or another fluid delivery conduit 106 can also be used to deliver, inject, or otherwise introduce a nutrient solution to the filter housing 108 after step 1A. The nutrient solution can include water, growth media, or a combination thereof. The fluid delivery conduit 106 can continuously or periodically expose the filter surface 118 to the nutrient solution.

The same fluid delivery conduit 106 or another fluid delivery conduit 106 can also be used to deliver, inject, or otherwise introduce a buffer solution 124 to the bacteria 102 captured on the filter surface 118 in step 1B. The buffer solution 124 can include, but is not limited to, a lysing agent 120, a β-lactamase substrate 128, and a β-lactamase activator 132. As will be discussed below, the buffer solution 124 can also include a β-lactamase inhibitor 134.

The lysing agent 120 can lyse or cause cells of the bacteria 102 captured on the filter surface 118 to release β-lactam antibiotic hydrolyzing enzymes 122, if any, on to the filter surface 118 or into the fluid environment or media surrounding the filter 110. For example, the lysing agent 120 can lyse the cells of the bacteria 102 and release β-lactam antibiotic hydrolyzing enzymes 122, if any, into the buffer solution 124 collected in the filter housing 108.

The lysing agent 120 can comprise one or more enzymes or lysozymes. In another embodiment, the lysing agent 120 can comprise one or more detergents designed to solubilize cell components of the bacteria 102. In other embodiments, the lysing agent 120 can comprise solutions having a high salt concentration designed to osmotically shock the cells of the bacteria 102. Moreover, the lysing agent 120 can comprise one or more commercial lysis reagents such as the Bacterial Protein Extraction Reagent (B-PER™) manufactured by ThermoFisher Scientific®. Furthermore, the lysing agent 120 can comprise any combination of the enzymes, detergents, high-salt solutions, sodium hydroxide, or reagents mentioned heretofore. In another embodiment, the bacteria 102 can be lysed by sonication.

The β-lactam antibiotic hydrolyzing enzymes 122 can comprise at least one of an extended spectrum β-lactamase, an inhibitor-resistant β-lactamase, and an AmpC-type β-lactamase. In another embodiment, the β-lactam antibiotic hydrolyzing enzymes 122 can be a carbapenemase.

The β-lactamase substrate 128 can comprise at least one of carbapenems, cephamycins, penicillins, cephalosporins, and monobactams in a buffered solution.

The β-lactamase activator 132 can be used as a co-factor to initiate or enhance the enzyme activity of the β-lactam antibiotic hydrolyzing enzymes 122. The β-lactamase activator 132 can include at least one of a divalent cation, a divalent cation salt, or a combination thereof.

The buffer solution 124 and the β-lactam antibiotic hydrolyzing enzymes 122 can mix or be collected in the filter housing 108 to form a reaction mixture 126 in step 1C. The filter housing 108 comprising the reaction mixture 126 can be heated to a reaction temperature 130 of between 20° C. and 40° C. and allowed to incubate for an incubation period in step 1C. In one embodiment, the filter housing 108 can be heated to a reaction temperature 130 of approximately 37° C. and allowed to incubate for 10 to 120 minutes.

The incubation period can also be adjusted based on the amount or volume of the sample 104. For example, the incubation period can be increased when the volume of the sample 104 is below a threshold amount.

One advantage of incubating the filter housing 108 comprising the reaction mixture 126 is to increase the sensitivity of the system 100A to low or subthreshold levels of the suspected bacteria 102. For example, incubating the filter 110 can allow the system 100A to increase its level of detection by promoting bacterial growth.

In an alternative embodiment not shown in the figures but contemplated by this disclosure, the filter 110 comprising the captured bacteria 102 can be incubated after step 1A between 30 minutes and four hours prior to introducing the buffer solution 124. In other embodiments, the filter 110 comprising the captured bacteria 102 can be incubated after step 1A for greater than four hours prior to introducing the buffer solution 124. The purpose of this pre-incubation is to allow for bacterial growth on the filter surface 118 and increase the level of detection of the system 100A.

As seen in FIG. 1A, a β-lactamase inhibitor 134 can also be added to the reaction mixture 126. The β-lactamase inhibitor 134 can be added as part of the buffer solution 124. The β-lactamase inhibitor 134 can serve as an internal control and validate the presence of certain β-lactamases. The β-lactamase inhibitor 134 can also be used to determine if whether the β-lactamase inhibitor 134 can act as a therapeutic to inhibit the β-lactam antibiotic hydrolyzing enzymes 122 within the patient. The β-lactamase inhibitor 134 can include, but is not limited to, tebipenem, 6-methylidene penem2, boron based transition state inhibitors (BATSIs), clavulanic acid, sulbactam, tazobactam, avibactam, relebactam, or a combination thereof.

After adding the β-lactamase inhibitor 134 to the reaction mixture 126 or after incubating the filter housing 108 in step 1C, a sensor 112 can be exposed to the reaction mixture 126 to analyze the reaction mixture 126 in either steps 1D(i) or 1D(ii). The sensor 112 will be discussed in more detail in the following sections.

As shown in step 1D(i) of FIG. 1A, the sensor 112 can be integrated with the filter housing 108, the filter 110, or a combination thereof. In this embodiment, the sensor 112 can continuously be exposed to the solution in the filter housing 108 and can begin to analyze the reaction mixture 126 as the buffer solution 124 is introduced to the bacteria 102 on the filter 110. In this and other embodiments, the filter 110, the filter housing 108, the sensor 134, the fluid delivery conduit 106, or a combination thereof can all be part of one device or apparatus. For example, the filter 110, the filter housing 108, the sensor 134, the fluid delivery conduit 106, or a combination thereof can be components of a handheld device. In other embodiments, the filter 110, the filter housing 108, the sensor 134, the fluid delivery conduit 106, or a combination thereof can be components of a kit or diagnostic assembly. In another embodiment not shown in the figures but contemplated by this disclosure, an aliquot or portion of the reaction mixture 126 can be injected, dropped, or otherwise introduced to a layer or receiving surface of the sensor 112.

In an alternative embodiment shown as step 1D(ii), the reaction mixture 126 can be analyzed by inserting a portion of the sensor 112 directly into the reaction mixture 126. In this and other embodiments, the sensor 112 and the parameter analyzer 114 can be coupled to the same substrate 116.

The sensor 112 can monitor a change in a solution characteristic of the reaction mixture 126. The solution characteristic can refer to one or more attributes of the solution making up the reaction mixture 126. For example, the solution characteristic can include a concentration of a solute, an absolute number or molecular count of solutes in solution, a solution temperature, or a combination thereof. For example, the solution characteristic can refer to the amount or concentration of ions, organic molecules such as amino acids, vitamins or glucose, minerals, or other inorganic compounds in the reaction mixture 126.

A change in the solution characteristic can cause a change in the electrical characteristic of the sensor 112. The parameter analyzer 114 can detect a change in the electrical characteristic of the sensor 112 exposed to the reaction mixture 126 in step 1E. The parameter analyzer 114 can monitor or detect a change in the electrical characteristic of the sensor 112 to detect the presence of β-lactam antibiotic hydrolyzing bacteria 136 in the sample 104 originally introduced.

The β-lactam antibiotic hydrolyzing bacteria 136 can include any bacteria capable of hydrolyzing a chemical compound or agent comprising a β-lactam ring in its molecular structure. The β-lactam antibiotic hydrolyzing bacteria 136 can also include any bacteria capable of producing β-lactam antibiotic hydrolyzing enzymes. The β-lactam antibiotic hydrolyzing bacteria 136 includes bacteria from at least one of the genera *Acinetobacter, Aeromonas, Bacillus, Bacteriodes, Citrobacter, Enterobacter, Escherichia, Klebsiella, Morganella, Pandoraea, Proteus, Providencia, Pseudomonas, Ralstonia, Raoultella, Salmonella, Serratia, Shewanella, Shigella*, and *Strenotrophomonas*.

The solution characteristic can vary as a result of the reaction between the β-lactam antibiotic hydrolyzing enzymes 122, resulting from the lysing of the β-lactam antibiotic hydrolyzing bacteria 136, and the β-lactamase substrate 128. For example, the solution characteristic can be a direct or indirect byproduct of the reaction between the β-lactam antibiotic hydrolyzing enzymes 122 and the β-lactamase substrate 128. The solution characteristic can vary as a result of ions, organic molecules, or minerals produced by, consumed by, or otherwise attributed to the reaction between the β-lactam antibiotic hydrolyzing enzymes 122 and the β-lactamase substrate 128. For example, the solution characteristic can change as hydrogen ions ($H^+$) are produced as a result of the reaction between the β-lactam antibiotic hydrolyzing enzymes 122 and the β-lactamase substrate 128.

For example, the sensor 112 can be a pH sensor and exposing the pH sensor to the reaction mixture 126 can reveal a decrease in the pH of the reaction mixture 126 over time as the concentration of hydrogen ions ($H^+$) increases in the reaction mixture 126 as a result of the reaction between the β-lactam antibiotic hydrolyzing enzymes 122 and the β-lactamase substrate 128. The decrease in the pH of the reaction mixture 126 as measured by a pH sensor 112 can reveal the presence of β-lactam antibiotic hydrolyzing bacteria 136 in the sample 104 originally introduced.

In an alternative embodiment, the sample 104 originally introduced can comprise bacteria 102 without resistance to antibiotics or with no ability to hydrolyze β-lactam antibiotics. In this embodiment, introducing a buffer solution 124 comprising a lysing agent 120 and one or more β-lactamase substrates 128 to such bacteria would not result in the same type of solution characteristic change as that seen in reaction mixtures 126 made from samples 104 containing β-lactam antibiotic hydrolyzing bacteria 136.

As shown in FIG. 1A, the parameter analyzer 114 can be fabricated on the same substrate 116 as the sensor 112. In other embodiments, the parameter analyzer 114 can be a standalone unit or meter coupled to the sensor 112. The parameter analyzer 114, the sensor 112, or a combination thereof can detect the presence of the β-lactam antibiotic hydrolyzing bacteria 136 within a detection window 138. In some embodiments, the detection window 138 can be between one minute and five minutes. In other embodiments, the detection window 138 can be between 60 minutes and 120 minutes. In yet additional embodiments, the detection window 138 can be between five minutes and 60 minutes. For example, the sensor 112 can monitor the solution characteristic of the reaction mixture 126 between one minute and 120 minutes in order detect the presence of the β-lactam antibiotic hydrolyzing bacteria 136 in the sample 104 originally introduced.

The parameter analyzer 114 can also be connected to or communicatively coupled to a display 140 or display component configured to provide a result of the detection or a read-out of the electrical characteristic of the sensor 112. In certain embodiments, the parameter analyzer 114 can be a mobile device, a handheld device, a tablet device, or a computing device such as a laptop or desktop computer and the display 140 can be a mobile device display, a handheld device display, a tablet display, or a laptop or desktop monitor. In one embodiment, the parameter analyzer 114 can display a result indicating the presence of β-lactam antibiotic hydrolyzing bacteria 136 in the sample 104 via the display 140 of the parameter analyzer 114. In another embodiment, the parameter analyzer 114 can wirelessly communicate a result indicating the presence of β-lactam antibiotic hydrolyzing bacteria 136 in the sample 104 to a computing device having the display 140.

In one embodiment, the parameter analyzer 114 can be a voltage meter. In other embodiments, the parameter analyzer 114 can be, but is not limited to, a multimeter, a source meter, an ammeter, a capacitance analyzer, or a combination thereof.

The electrical characteristic of the sensor 112 can include, but is not limited to, a voltage, an impedance, a current, a capacitance, a resistance, a resonant frequency, a noise level, a level of induction, or a combination thereof of the sensor 112. For example, the electrical characteristic can be an internal voltage or current of the sensor 112. The change in the electrical characteristic can include, but is not limited to, a voltage change, an impedance change, a current change, a capacitance change, a resistance change, a change in resonant frequency, a noise level change, an induction change, or a combination thereof of the sensor 112.

The steps depicted in FIG. 1A do not require the particular order shown to achieve the desired result. Moreover, certain steps or processes may be omitted or occur in parallel in order to achieve the desired result.

Figure 1B:
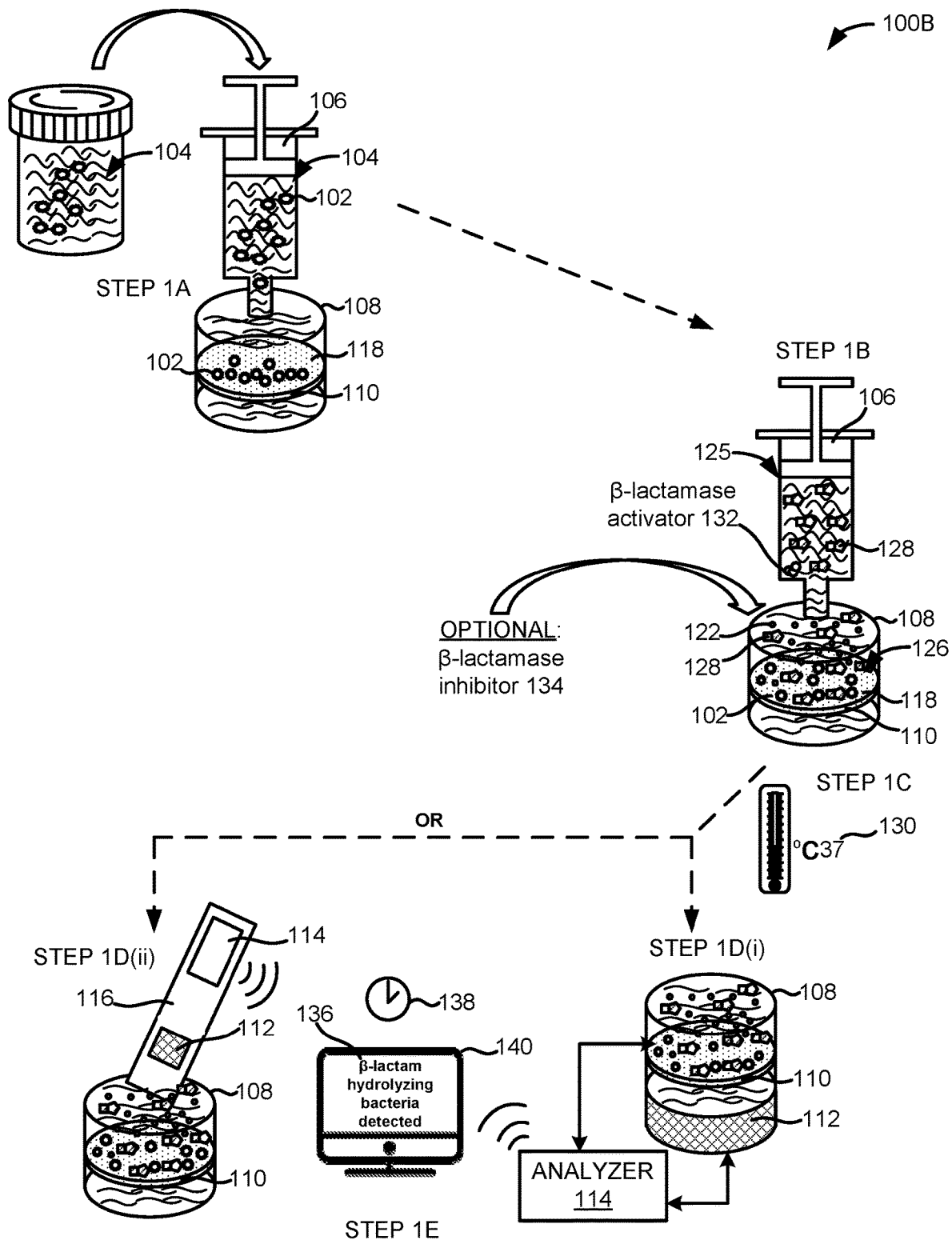
FIG. 1B illustrates another embodiment of a system and a method of operation thereof for detecting β-lactam antibiotic hydrolyzing bacteria in a sample.

FIG. 1B illustrates another embodiment of a system 100B for detecting β-lactam antibiotic hydrolyzing bacteria 136 in a sample 104. In one embodiment, the system 100B can comprise a fluid delivery conduit 106, a filter housing 108 containing a filter 110, a sensor 112, and a parameter analyzer 114. The sensor 112 can be located on a substrate 116.

The substrate 116 can be comprised of a polymer or polymeric material, a metal, a ceramic, a semiconductor layer, an oxide layer, an insulator, or a combination thereof. As shown in FIG. 1B, the parameter analyzer 114 can be integrated into one device with the sensor 112. For example, the parameter analyzer 114 can be fabricated on the same substrate 116 as the sensor 112. In other embodiments, the parameter analyzer 114 can be a standalone unit or device coupled to the sensor 112. The sensor 112 will be discussed in more detail in the sections that follow.

The sample 104 can comprise at least one of a biological sample, a bodily fluid, and a bacterial culture derived from the biological sample or the bodily fluid. The bodily fluid can comprise urine, blood, serum, plasma, saliva, sputum, semen, breast milk, joint fluid, spinal fluid, wound material, mucus, fluid accompanying stool, re-suspended rectal or wound swabs, or a combination thereof.

The sample 104 can carry or contain bacteria 102. The bacteria 102 can include gram negative bacteria, gram positive bacteria, or a combination thereof. The bacteria 102 can also include antibiotic resistant bacteria, antibiotic susceptible or intermediate resistant bacteria, or a combination thereof. For example, the bacteria 102 can include β-lactam antibiotic hydrolyzing bacteria 136.

At least some of the bacteria 102 can secrete β-lactam antibiotic hydrolyzing enzymes 122. The β-lactam antibiotic hydrolyzing enzymes 122 can comprise at least one of an extended spectrum β-lactamase, an inhibitor-resistant β-lactamase, and an AmpC-type β-lactamase. In another embodiment, the β-lactam antibiotic hydrolyzing enzymes 122 can be a carbapenemase The fluid delivery conduit 106 can be a tube or channel for delivering buffers, reagents, fluid samples including the sample 104 to devices, apparatus, or containers in the system. For example, as shown in FIG. 1B, the fluid delivery conduit 106 can be or refer to part of a pump such as a syringe pump. In other embodiments, the fluid delivery conduit 106 can include or refer to at least part of a hydraulic pump, a pneumatic pump, a peristaltic pump, a vacuum pump, or a combination thereof. In additional embodiments, the fluid delivery conduit 106 can include or refer to at least part of an injection cartridge, a microfluidic channel, a pipette, a reaction tube, a capillary, a test tube, or a combination thereof. The fluid delivery conduit 106 can be part of a vacuum system configured to draw fluid to or through the filter 110 under vacuum. Moreover, the fluid delivery conduit 106 can include or refer to at least part of a multichannel delivery device or pipette.

The filter housing 108 can be a container or vessel configured to secure or enclose the filter 110. For example, the filter housing 108 can be a protective chamber. The protective chamber can be an electrically isolated environment. The protective chamber can also be a temperature controlled chamber, a light controlled chamber, or a combination thereof.

The filter 110 can have a filter surface 118. The filter 110 can trap or isolate the bacteria 102 by depositing or capturing the bacteria 102 on to the filter surface 118. The filter surface 118 can be an external surface, an internal surface extending into the filter 110, or a combination thereof. The filter 110 can be made of, but is not limited to, cellulose acetate, regenerated cellulose, nylon, polystyrene, polyvinylidene fluoride (PVDF), polyethersulfone (PES), polytetrafluoroethylene (PTFE), glass microfiber, or a combination thereof.

In one embodiment, the filter 110 can have filter pores of sequentially smaller pore size. For example, the filter 110 can have larger filter pores at the top of the filter and progressively smaller filters pores toward the bottom of the filter. In another embodiment, the filter 110 can have filter pores of a similar pore size throughout the entire filter. In these embodiments, the filter surface 118 can be the surface of the pores. In another embodiment, the filter 110 can be a mesh or matrix structure and the filter surface 118 can be a mesh or matrix surface.

The filter 110 can be a non-clogging filter such as a high-capacity filter. Although not shown in FIG. 1B, it is contemplated by this disclosure that the filter 110 can refer to a plurality of filters in a stacked arrangement.

The filter 110 can capture and hold the bacteria 102 when a sample 104 comprising or carrying the bacteria 102 is introduced to the filter 110 in step 1A shown in FIG. 1B. For example, the sample 104 can be introduced to the filter 110 when the sample 104 is poured over the filter 110 or injected through the filter 110. The filter 110 can isolate or separate the bacteria 102 or other molecules or cells from the supernatant of the sample 104.

In one embodiment, the filter housing 108 can have at least one opening which allows fluid or supernatant from the sample 104 to evacuate the filter housing 108. For example, step 1A can include the additional step of discarding the fluid or supernatant from the sample 104 through the opening after isolating the bacteria 102 on the filter surface 118. Although the filter housing 108 is shown as a separate container or apparatus from the fluid delivery conduit 106, it is contemplated by this disclosure that the filter housing 108 and the filter 110 can be integrated with the fluid delivery conduit 106 or serve as an attachment to the fluid delivery conduit 106. For example, the filter housing 108 can be a part of a syringe serving as the fluid delivery conduit 106. In another example, the filter housing 108 can be a syringe filter and the filter surface 118 can be a filter surface within the syringe filter.

In an alternative embodiment not shown in FIG. 1B, a stimulus solution can be added to the sample 104 before introducing the sample 104 to the filter 110. The stimulus solution can be a nutrient or growth solution. The stimulus solution can be a super nutrient solution.

The sample 104 can also be pre-filtered in a step before step 1A. This pre-filtering step can involve filtering the sample 104 using an additional filter, a microfluidic filter, or a combination thereof to filter out other larger cellular components including blood cells or epithelial cells from the sample 104 when the sample 104 is composed of bodily fluid.

The same fluid delivery conduit 106 or another fluid delivery conduit 106 can also be used to deliver, inject, or otherwise introduce a nutrient solution to the filter housing 108 after step 1A. The nutrient solution can include water, growth media, or a combination thereof. The fluid delivery conduit 106 can continuously or periodically expose the filter surface 118 to the nutrient solution.

The same fluid delivery conduit 106 or another fluid delivery conduit 106 can also be used to deliver, inject, or otherwise introduce a buffer solution 125 to the bacteria 102 captured on the filter surface 118 in step 1B. The buffer solution 125 can include, but is not limited to, a β-lactamase substrate 128, and a β-lactamase activator 132. As will be discussed below, the buffer solution 125 can also include a β-lactamase inhibitor 134.

The β-lactamase substrate 128 can comprise at least one of carbapenems, cephamycins, penicillins, cephalosporins, and monobactams in a buffered solution.

The β-lactamase activator 132 can be used as a co-factor to initiate or enhance the enzyme activity of the β-lactam antibiotic hydrolyzing enzymes 122. The β-lactamase activator 132 can include at least one of a divalent cation, a divalent cation salt, or a combination thereof.

The buffer solution 125 and the β-lactam antibiotic hydrolyzing enzymes 122 secreted by the bacteria 102 can mix or be collected in the filter housing 108 to form a reaction mixture 126 in step 1C. The filter housing 108 comprising the reaction mixture 126 can be heated to a reaction temperature 130 of between 20° C. and 40° C. and allowed to incubate for an incubation period in step 1C. In one embodiment, the filter housing 108 can be heated to a reaction temperature 130 of approximately 37° C. and allowed to incubate for 10 to 120 minutes.

The incubation period can also be adjusted based on the amount or volume of the sample 104. For example, the incubation period can be increased when the volume of the sample 104 is below a threshold amount.

One advantage of incubating the filter housing 108 comprising the reaction mixture 126 is to increase the sensitivity of the system 100B to low or subthreshold levels of the suspected bacteria 102. For example, incubating the filter 110 can allow the system 100B to increase its level of detection by promoting bacterial growth.

In an alternative embodiment not shown in the figures but contemplated by this disclosure, the filter 110 comprising the captured bacteria 102 can be incubated after step 1A between 30 minutes and four hours prior to introducing the buffer solution 125. In other embodiments, the filter 110 comprising the captured bacteria 102 can be incubated after step 1A for greater than four hours prior to introducing the buffer solution 125. The purpose of this pre-incubation is to allow for bacterial growth on the filter surface 118 and increase the level of detection of the system 100B.

As seen in FIG. 1B, a β-lactamase inhibitor 134 can also be added to the reaction mixture 126. The β-lactamase inhibitor 134 can be added as part of the buffer solution 125. The β-lactamase inhibitor 134 can serve as an internal control and validate the presence of certain β-lactamases. The β-lactamase inhibitor 134 can also be used to determine if whether the β-lactamase inhibitor 134 can act as a therapeutic to inhibit the β-lactam antibiotic hydrolyzing enzymes 122 within the patient. The β-lactamase inhibitor 134 can include, but is not limited to, tebipenem, 6-methylidene penem2, boron based transition state inhibitors (BATSIs), clavulanic acid, sulbactam, tazobactam, avibactam, relebactam, or a combination thereof.

After adding the β-lactamase inhibitor 134 to the reaction mixture 126 or after incubating the filter housing 108 in step 1C, a sensor 112 can be exposed to the reaction mixture 126 to analyze the reaction mixture 126 in either steps 1D(i) or 1D(ii). The sensor 112 will be discussed in more detail in the following sections.

As shown in step 1D(i) of FIG. 1B, the sensor 112 can be integrated with the filter housing 108, the filter 110, or a combination thereof. In this embodiment, the sensor 112 can continuously be exposed to the solution in the filter housing 108 and can begin to analyze the reaction mixture 126 as the buffer solution 125 is introduced to the bacteria 102 on the filter 110. In this and other embodiments, the filter 110, the filter housing 108, the sensor 134, the fluid delivery conduit 106, or a combination thereof can all be part of one device or apparatus. For example, the filter 110, the filter housing 108, the sensor 134, the fluid delivery conduit 106, or a combination thereof can be components of a handheld device. In other embodiments, the filter 110, the filter housing 108, the sensor 134, the fluid delivery conduit 106, or a combination thereof can be components of a kit or diagnostic assembly. In another embodiment not shown in the figures but contemplated by this disclosure, an aliquot or portion of the reaction mixture 126 can be injected, dropped, or otherwise introduced to a layer or receiving surface of the sensor 112.

In an alternative embodiment shown as step 1D(ii), the reaction mixture 126 can be analyzed by inserting a portion of the sensor 112 directly into the reaction mixture 126. In this and other embodiments, the sensor 112 and the parameter analyzer 114 can be coupled to the same substrate 116.

The sensor 112 can monitor a change in a solution characteristic of the reaction mixture 126. The solution characteristic can refer to one or more attributes of the solution making up the reaction mixture 126. For example, the solution characteristic can include a concentration of a solute, an absolute number or molecular count of solutes in solution, a solution temperature, or a combination thereof. For example, the solution characteristic can refer to the amount or concentration of ions, organic molecules such as amino acids, vitamins or glucose, minerals, or other inorganic compounds in the reaction mixture 126.

A change in the solution characteristic can cause a change in the electrical characteristic of the sensor 112. The parameter analyzer 114 can detect a change in the electrical characteristic of the sensor 112 exposed to the reaction mixture 126 in step 1E. The parameter analyzer 114 can monitor or detect a change in the electrical characteristic of the sensor 112 to detect the presence of β-lactam antibiotic hydrolyzing bacteria 136 in the sample 104 originally introduced.

The β-lactam antibiotic hydrolyzing bacteria 136 can include any bacteria capable of hydrolyzing a chemical compound or agent comprising a β-lactam ring in its molecular structure. The β-lactam antibiotic hydrolyzing bacteria 136 can also include any bacteria capable of producing β-lactam antibiotic hydrolyzing enzymes. The β-lactam antibiotic hydrolyzing bacteria 136 includes bacteria from at least one of the genera *Acinetobacter, Aeromonas, Bacillus, Bacteriodes, Citrobacter, Enterobacter, Escherichia, Klebsiella, Morganella, Pandoraea, Proteus, Providencia, Pseudomonas, Ralstonia, Raoultella, Salmonella, Serratia, Shewanella, Shigella*, and *Strenotrophomonas*.

The solution characteristic can vary as a result of the reaction between the β-lactam antibiotic hydrolyzing enzymes 122 secreted by the β-lactam antibiotic hydrolyzing bacteria 136 (if any) and the β-lactamase substrate 128. For example, the solution characteristic can be a direct or indirect byproduct of the reaction between the β-lactam antibiotic hydrolyzing enzymes 122 and the β-lactamase substrate 128. The solution characteristic can vary as a result of ions, organic molecules, or minerals produced by, consumed by, or otherwise attributed to the reaction between the β-lactam antibiotic hydrolyzing enzymes 122 and the β-lactamase substrate 128. For example, the solution characteristic can change as hydrogen ions ($H^+$) are produced as a result of the reaction between the β-lactam antibiotic hydrolyzing enzymes 122 and the β-lactamase substrate 128.

For example, the sensor 112 can be a pH sensor and exposing the pH sensor to the reaction mixture 126 can reveal a decrease in the pH of the reaction mixture 126 over time as the concentration of hydrogen ions ($H^+$) increases in the reaction mixture 126 as a result of the reaction between the β-lactam antibiotic hydrolyzing enzymes 122 and the β-lactamase substrate 128. The decrease in the pH of the reaction mixture 126 as measured by a pH sensor 112 can reveal the presence of β-lactam antibiotic hydrolyzing bacteria 136 in the sample 104 originally introduced.

In an alternative embodiment, the sample 104 originally introduced can comprise bacteria 102 without resistance to antibiotics or with no ability to hydrolyze β-lactam antibiotics. In this embodiment, introducing a buffer solution 125 comprising one or more β-lactamase substrates 128 to such bacteria would not result in the same type of solution characteristic change as that seen in reaction mixtures 126 made from samples 104 containing β-lactam antibiotic hydrolyzing bacteria 136.

As shown in FIG. 1B, the parameter analyzer 114 can be fabricated on the same substrate 116 as the sensor 112. In other embodiments, the parameter analyzer 114 can be a standalone unit or meter coupled to the sensor 112. The parameter analyzer 114, the sensor 112, or a combination thereof can detect the presence of the β-lactam antibiotic hydrolyzing bacteria 136 within a detection window 138. In some embodiments, the detection window 138 can be between one minute and five minutes. In other embodiments, the detection window 138 can be between 60 minutes and 120 minutes. In yet additional embodiments, the detection window 138 can be between five minutes and 60 minutes. For example, the sensor 112 can monitor the solution characteristic of the reaction mixture 126 between one minute and 120 minutes in order detect the presence of the β-lactam antibiotic hydrolyzing bacteria 136 in the sample 104 originally introduced.

The parameter analyzer 114 can also be connected to or communicatively coupled to a display 140 or display component configured to provide a result of the detection or a read-out of the electrical characteristic of the sensor 112. In certain embodiments, the parameter analyzer 114 can be a mobile device, a handheld device, a tablet device, or a computing device such as a laptop or desktop computer and the display 140 can be a mobile device display, a handheld device display, a tablet display, or a laptop or desktop monitor. In one embodiment, the parameter analyzer 114 can display a result indicating the presence of β-lactam antibiotic hydrolyzing bacteria 136 in the sample 104 via the display 140 of the parameter analyzer 114. In another embodiment, the parameter analyzer 114 can wirelessly communicate a result indicating the presence of β-lactam antibiotic hydrolyzing bacteria 136 in the sample 104 to a computing device having the display 140.

In one embodiment, the parameter analyzer 114 can be a voltage meter. In other embodiments, the parameter analyzer 114 can be, but is not limited to, a multimeter, a source meter, an ammeter, a capacitance analyzer, or a combination thereof.

The electrical characteristic of the sensor 112 can include, but is not limited to, a voltage, an impedance, a current, a capacitance, a resistance, a resonant frequency, a noise level, a level of induction, or a combination thereof of the sensor 112. For example, the electrical characteristic can be an internal voltage or current of the sensor 112. The change in the electrical characteristic can include, but is not limited to, a voltage change, an impedance change, a current change, a capacitance change, a resistance change, a change in resonant frequency, a noise level change, an induction change, or a combination thereof of the sensor 112.

The steps depicted in FIG. 1B do not require the particular order shown to achieve the desired result. Moreover, certain steps or processes may be omitted or occur in parallel in order to achieve the desired result.

Figure 2:
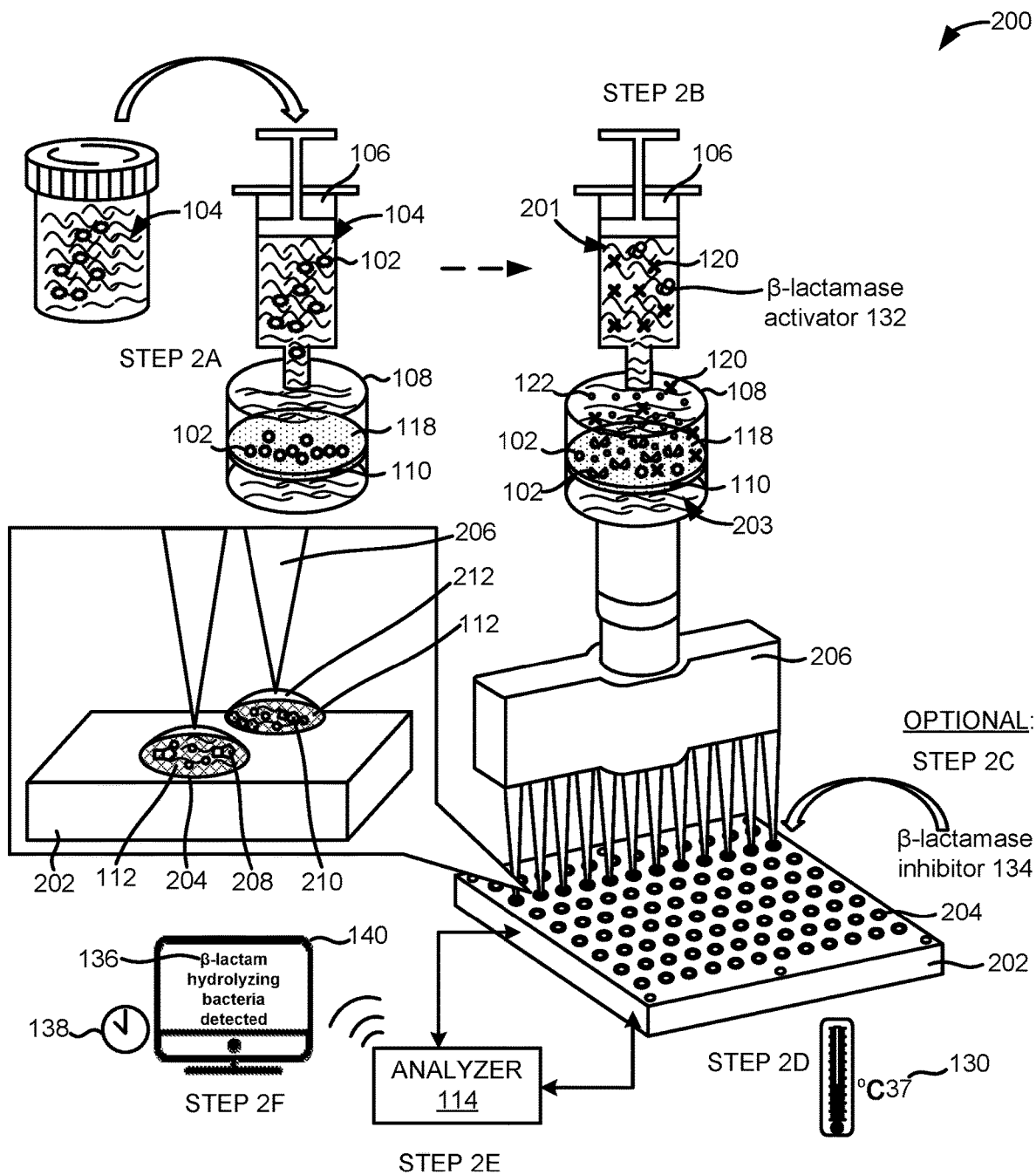
FIG. 2 illustrates yet another embodiment of a system and a method of operation thereof for detecting β-lactam antibiotic hydrolyzing bacteria in a sample.

FIG. 2 illustrates an embodiment of a system 200 for detecting β-lactam antibiotic hydrolyzing bacteria 136 in a sample 104. In one embodiment, the system 200 can comprise a fluid delivery conduit 106, a filter housing 108 containing a filter 110, a plurality of sensors 112, a parameter analyzer 114, a well plate 202 comprising a plurality of reaction wells 204, a multichannel delivery device 206, or a combination thereof.

In one embodiment, the plurality of sensors 112 can be integrated with the well plate 202 and each of the reaction wells 204 can have a sensor 112 embedded in the reaction well 204. In another embodiment contemplated by this disclosure but not shown in FIG. 2, the plurality of sensors 112 can be separate from the well plate 202 and can be exposed to fluid or samples in the reaction wells 204 of the well plate 202.

The well plate 202 can be comprised of or fabricated using polymers or polymeric material, a metal, a ceramic, a semiconductor layer, an insulator, an oxide layer, or a combination thereof. The parameter analyzer 114 can be a standalone unit or device coupled to the well plate 202 or the sensors 112 embedded in the reaction wells 204 of the well plate. In other embodiments, the parameter analyzer 114 can be integrated into one device with the well plate 202, the sensors 112, or a combination thereof.

The sample 104 can comprise at least one of a biological sample, a bodily fluid, and a bacterial culture derived from the biological sample or the bodily fluid. The bodily fluid can comprise urine, blood, serum, plasma, saliva, sputum, semen, breast milk, joint fluid, spinal fluid, wound material, mucus, fluid accompanying stool, re-suspended rectal or wound swabs, or a combination thereof.

The sample 104 can carry or contain bacteria 102. The bacteria 102 can include gram negative bacteria, gram positive bacteria, or a combination thereof. The bacteria 102 can also include antibiotic resistant bacteria, antibiotic susceptible or intermediate resistant bacteria, or a combination thereof. For example, the bacteria 102 can include β-lactam antibiotic hydrolyzing bacteria 136.

The fluid delivery conduit 106 can be a tube or channel for delivering buffers, reagents, fluid samples including the sample 104 to devices, apparatus, or containers in the system. For example, as shown in FIG. 2, the fluid delivery conduit 106 can be or refer to part of a pump such as a syringe pump. In other embodiments, the fluid delivery conduit 106 can include or refer to at least part of a hydraulic pump, a pneumatic pump, or a combination thereof. In additional embodiments, the fluid delivery conduit 106 can include or refer to at least part of an injection cartridge, a microfluidic or macrofluidic channel, a pipette, a reaction tube, a capillary, a test tube, or a combination thereof.

The fluid delivery conduit 106 can be connected to or integrated with the multichannel delivery device 206. In one embodiment, the fluid delivery conduit 106 can refer to or comprise a portion of the multichannel delivery device 206. For example, the multichannel delivery device 206 can refer to or comprise a multichannel syringe, handheld pipette, pipette system or station, or a combination thereof. More specifically, the fluid delivery conduit 106 can refer to or comprise upstream conduits or channels of the multichannel delivery device 206.

In other embodiments, the fluid delivery conduit 106 can refer to or comprise one or more separate devices from the multichannel delivery device 206. In these embodiments, the fluid delivery conduit 106 can be connected or in fluid communication with the multichannel delivery device 206 through tubes, pipes, channels, microfluidic channels, or a combination thereof.

The filter housing 108 can be a container or vessel configured to secure or enclose the filter 110. For example, the filter housing 108 can be a protective chamber. The protective chamber can be an electrically isolated environment. The protective chamber can also be a temperature controlled chamber, a light controlled chamber, or a combination thereof.

The filter 110 can have a filter surface 118. The filter 110 can trap or isolate the bacteria 102 by depositing or capturing the bacteria 102 on to the filter surface 118. The filter surface 118 can be an external surface, an internal surface extending into the filter 110, or a combination thereof. The filter 110 can be made of, but is not limited to, cellulose acetate, regenerated cellulose, nylon, polystyrene, polyvinylidene fluoride (PVDF), polyethersulfone (PES), polytetrafluoroethylene (PTFE), glass microfiber, or a combination thereof.

In one embodiment, the filter 110 can have filter pores of sequentially smaller pore size. For example, the filter 110 can have larger filter pores at the top of the filter and progressively smaller filters pores toward the bottom of the filter. In another embodiment, the filter 110 can have filter pores of a similar pore size throughout the entire filter. In these embodiments, the filter surface 118 can be the surface of the pores. In another embodiment, the filter 110 can be a mesh or matrix structure and the filter surface 118 can be a mesh or matrix surface.

The filter 110 can be a non-clogging filter such as a high-capacity filter. Although not shown in FIG. 2, it is contemplated by this disclosure that the filter 110 can refer to a plurality of filters in a stacked arrangement.

The filter 110 can capture and hold the bacteria 102 when a sample 104 comprising or carrying the bacteria 102 is introduced to the filter 110 in step 2A shown in FIG. 2. For example, the sample 104 can be introduced to the filter 110 when the sample 104 is poured over the filter 110 or injected through the filter 110. The filter 110 can isolate or separate the bacteria 102 or other molecules or cells from the supernatant of the sample 104.

In one embodiment, the filter housing 108 can have at least one opening which allows fluid or supernatant from the sample 104 to evacuate the filter housing 108. For example, step 2A can include the additional step of discarding the fluid or supernatant from the sample 104 through the opening after isolating the bacteria 102 on the filter surface 118. Although the filter housing 108 is shown as a separate container or apparatus from the fluid delivery conduit 106, it is contemplated by this disclosure that the filter housing 108 and the filter 110 can be integrated with the fluid delivery conduit 106 or serve as an attachment to the fluid delivery conduit 106. For example, the filter housing 108 can be a part of a syringe serving as the fluid delivery conduit 106. In another example, the filter housing 108 can be a syringe filter and the filter surface 118 can be a filter surface within the syringe filter.

In an alternative embodiment not shown in FIG. 2, a stimulus solution can be added to the sample 104 before introducing the sample 104 to the filter 110. The stimulus solution can be a nutrient or growth solution. The stimulus solution can be a super nutrient solution.

The sample 104 can also be pre-filtered in a step before step 2A. This pre-filtering step can involve filtering the sample 104 using an additional filter, a microfluidic filter, or a combination thereof to filter out other larger cellular components including blood cells or epithelial cells from the sample 104 when the sample 104 is composed of bodily fluid.

The same fluid delivery conduit 106 or another fluid delivery conduit 106 can also be used to deliver, inject, or otherwise introduce a nutrient solution to the filter housing 108 after step 2A. The nutrient solution can include water, growth media, or a combination thereof. The fluid delivery conduit 106 can continuously or periodically expose the filter surface 118 to the nutrient solution.

The same fluid delivery conduit 106 or another fluid delivery conduit 106 can also be used to deliver, inject, or otherwise introduce a reaction buffer 201 to the bacteria 102 captured on the filter surface 118 in step 2B. The reaction buffer 201 can include, but is not limited to, a lysing agent 120 and a β-lactamase activator 132.

The lysing agent 120 can lyse or cause cells of the bacteria 102 captured on the filter surface 118 to release β-lactam antibiotic hydrolyzing enzymes 122, if any, on to the filter surface 118 or into the fluid environment or media surrounding the filter 110. For example, the lysing agent 120 can lyse the cells of the bacteria 102 and release β-lactam antibiotic hydrolyzing enzymes 122, if any, into the solution in the filter housing 108.

The lysing agent 120 can comprise one or more enzymes or lysozymes. In another embodiment, the lysing agent 120 can comprise one or more detergents designed to solubilize cell components of the bacteria 102. In other embodiments, the lysing agent 120 can comprise solutions having a high salt concentration designed to osmotically shock the cells of the bacteria 102. Moreover, the lysing agent 120 can comprise one or more commercial lysis reagents such as the Bacterial Protein Extraction Reagent (B-PER™) manufactured by ThermoFisher Scientific®. Furthermore, the lysing agent 120 can comprise any combination of the enzymes, detergents, high-salt solutions, sodium hydroxide, or reagents mentioned heretofore. In another embodiment, the bacteria 102 can be lysed by sonication.

The β-lactam antibiotic hydrolyzing enzymes 122 can comprise at least one of an extended spectrum β-lactamase, an inhibitor-resistant β-lactamase, and an AmpC-type β-lactamase. In another embodiment, the β-lactam antibiotic hydrolyzing enzymes 122 can be a carbapenemase.

The β-lactamase activator 132 can be used as a co-factor to initiate or enhance the enzyme activity of the β-lactam antibiotic hydrolyzing enzymes 122. The β-lactamase activator 132 can include at least one of a divalent cation, a divalent cation salt, or a combination thereof.

The reaction buffer 201 and the β-lactam antibiotic hydrolyzing enzymes 122 can mix or be collected in the filter housing 108 to form a reaction effluent 203. In the example embodiment shown in FIG. 2, the multichannel delivery device 206 can be used to deliver, inject, or otherwise introduce a portion of the reaction effluent 203 to the reaction wells 204 of the well plate 202. The multichannel delivery device 206 can be in fluid communication with the filter housing 108, the filter 110 including the filter surface 118, the fluid delivery conduit 106, or a combination thereof.

For example, the fluid delivery conduit 106 and the multichannel delivery device 206 can refer to parts of the same multichannel syringe, pipette, or pipette system and the filter housing 108 and the filter 110 can refer to a syringe filter or a pipette filter embedded with or coupled to the syringe, pipette, or pipette system. In another example, the multichannel delivery device 206 can refer to a separate device than a device comprising the fluid delivery conduit 106.

Each of the reaction wells 204 of the well plate 202 can contain or be exposed to a β-lactamase substrate 128. For example, the β-lactamase substrate 128 can be injected or delivered to the reaction wells 204 prior to the multichannel delivery device 206 or another delivery device carrying or delivering the reaction effluent 203 to the reaction wells 204.

In the embodiment shown in the inset of FIG. 2, one reaction well 204 can contain a first β-lactamase substrate 208 and another reaction well 204 can contain a second β-lactamase substrate 210. The second β-lactamase substrate 210 can be different than the first β-lactamase substrate 208. For example, the first β-lactamase substrate 208 can be a carbapenem and the second β-lactamase substrate 210 can be penicillin. Any of the first β-lactamase substrate 208 or the second β-lactamase substrate 210 can include at least one of carbapenems, cephamycins, penicillins, cephalosporins, and monobactams. The β-lactamase substrate 208 can be suspended in a buffered solution or non-buffer solution or can be dried and solubilized by a portion of the reaction effluent 203.

In one embodiment, the multichannel delivery device 206 or another device can deliver or introduce the reaction effluent 203 into the plurality of reaction wells 204 simultaneously. In another embodiment, the multichannel delivery device 206 or another device can deliver or introduce the reaction effluent 203 into the plurality of reaction wells 204 sequentially or periodically.

As shown in the inset in FIG. 2, once the multichannel delivery device 206 has delivered or introduced the reaction effluent 203 into the plurality of reaction wells 204 containing the β-lactamase substrate 128, the solution in such reaction wells 204 can be referred to as a reaction mixture 212. For example, when the sample 104 contains β-lactam antibiotic hydrolyzing bacteria 136, the multichannel delivery device 206 can deliver or introduce β-lactam antibiotic hydrolyzing enzymes 122 released from the lysed β-lactam antibiotic hydrolyzing bacteria 136 as part of the reaction effluent 203 to the reaction wells 204 and the reaction mixture 212 can comprise at least the β-lactamase substrate 128 and the β-lactam antibiotic hydrolyzing enzymes 122 in solution. Alternatively, when the sample 104 does not contain β-lactam antibiotic hydrolyzing bacteria 136, the reaction mixture 212 can be devoid of β-lactam antibiotic hydrolyzing enzymes 122.

Although the well plate 202 is shown as a microtiter or a high throughput assay plate in FIG. 2, it is contemplated by this disclosure that the system 200 can substitute a microfluidic chip, a lab-on-a-chip (LOC), or a bio-microelectromechanical system (BioMEMS) for the well plate 202. In this embodiment, the reaction wells 204 can be micro or nano sized chambers on the chip or system.

In some embodiments, a β-lactamase inhibitor 134 can be added to the reaction mixture 212 in step 2C. The β-lactamase inhibitor 134 can serve as an internal control and validate the presence of β-lactamases. The β-lactamase inhibitor 134 can also be used to determine if whether the β-lactamase inhibitor 134 can act as a therapeutic to inhibit the β-lactam antibiotic hydrolyzing enzymes 122 within the patient. The β-lactamase inhibitor 134 can include, but is not limited to, tebipenem, 6-methylidene penem2, boron based transition state inhibitors (BATSIs), clavulanic acid, sulbactam, tazobactam, avibactam, relebactam, or a combination thereof.

In the embodiment shown in FIG. 2, each of the reaction wells 204 can contain or be in fluid communication with a sensor 112. For example, as shown in FIG. 2, the sensors 112 can be embedded in the well plate 202. The well plate 202 can comprise active reaction wells, control wells, or a combination thereof. The active reaction wells can each contain at least one β-lactamase substrate 128. The control wells can contain no β-lactamase substrate or only a buffered or non-buffered solution.

The reaction wells 204 can be divots, indentations, or openings on the surface of a substrate serving as the well plate 202. In another embodiment, the reaction wells 204 can be individual compartments coupled to or extending out from a substrate or base layer. The reaction wells 204 can also be shaped as a hemisphere having a rounded bottom, a cuboid or cylinder having a flat or planar bottom, a cone, a frustoconical, or a combination thereof. The reaction wells 204 can also be covered by a well coating, such as an acidic or basic coating.

The entire well plate 202 or one or more individual reaction wells 204 comprising the reaction mixture 212 can be heated to a reaction temperature 130 of between 30° C. and 40° C. and allowed to incubate for an incubation period in step 2D. For example, the well plate 202 or one or more individual reaction wells 204 can be heated to a reaction temperature 130 of approximately 37° C. and allowed to incubate for 10 to 120 minutes upon introduction of the β-lactam antibiotic hydrolyzing enzymes 122.

The incubation period can also be adjusted based on the amount or volume of the sample 104. For example, the incubation period can be increased when the volume of the sample 104 is below a threshold amount.

One advantage of incubating the well plate 202 or the reaction wells 204 is to increase the sensitivity of the system 200 to small amounts of the suspected bacteria 102. For example, incubating the filter 110 can allow the system 200 to reduce its level of detection.

In an alternative embodiment not shown in the figures but contemplated by this disclosure, the filter 110 comprising the captured bacteria 102 can be incubated after step 2A between 30 minutes and four hours prior to introducing the lysing agent 120. The purpose of this pre-incubation is to allow for bacterial growth on the filter surface 118 and increase the level of detection of the system 200.

The sensors 112 can be continuously exposed to the reaction mixture 212 comprising the β-lactam antibiotic hydrolyzing enzymes 122 and the β-lactamase substrate 128. For example, the sensors 112 can be continuously exposed to the reaction mixture 212 when the sensors 112 are integrated with the well plate 202 or the reaction wells 204.

In another embodiment not shown in FIG. 2 but contemplated by this disclosure, a portion of a sensor 112 can be inserted into a reaction well 204 to analyze the solution characteristic of the reaction mixture 212 in the reaction well 204. For example, the same sensor 112 can be inserted into each of the reaction wells 204 of one or more well plates 302 to analyze the solution characteristics of the reaction mixtures 212 in the reaction wells 204. Alternatively, different sensors 112 can be inserted into different reaction wells 204 to analyze the solution characteristics of the reaction mixtures 212 in the reaction wells 204.

Each of the sensors 112 can monitor a change in the solution characteristic of the reaction mixtures 212 in the reaction wells 204. The solution characteristic can refer to one or more attributes of the reaction mixture 212 comprising the β-lactam antibiotic hydrolyzing enzymes 122 and the β-lactamase substrate 128. For example, the solution characteristic can include a concentration of a solute, an absolute number or molecular count of solutes in solution, a solution temperature, or a combination thereof. For example, the solution characteristic can refer to the amount or concentration of ions, organic molecules such as amino acids, vitamins or glucose, minerals, or other inorganic compounds in the reaction mixture 212 in each of the reaction wells 204.

A change in the solution characteristic can cause a change in the electrical characteristic of the sensor 112. The parameter analyzer 114 can detect a change in the electrical characteristic of the sensor 112 exposed to the solution in the reaction wells 204 in step 2E. The parameter analyzer 114 can monitor or detect a change in the electrical characteristic of the sensor 112 to detect the presence of β-lactam antibiotic hydrolyzing bacteria 136 in the sample 104 originally introduced.

The β-lactam antibiotic hydrolyzing bacteria 136 can include any bacteria capable of hydrolyzing a chemical compound or agent comprising a β-lactam ring in its molecular structure. The β-lactam antibiotic hydrolyzing bacteria 136 can also include any bacteria capable of producing β-lactam antibiotic hydrolyzing enzymes. The β-lactam antibiotic hydrolyzing bacteria 136 includes bacteria from at least one of the genera *Acinetobacter, Aeromonas, Bacillus, Bacteriodes, Citrobacter, Enterobacter, Escherichia, Klebsiella, Morganella, Pandoraea, Proteus, Providencia, Pseudomonas, Ralstonia, Raoultella, Salmonella, Serratia, Shewanella, Shigella*, and *Strenotrophomonas*.

The solution characteristic can vary as a result of the reaction between the β-lactam antibiotic hydrolyzing enzymes 122 and the β-lactamase substrate 128, such as the first β-lactamase substrate 208 or the second β-lactamase substrate 210, in the reaction mixture 212. For example, the solution characteristic can be a direct or indirect byproduct of the reaction between the β-lactam antibiotic hydrolyzing enzymes 122 and the β-lactamase substrate 128 in the reaction mixture 212. The solution characteristic can vary as a result of ions, organic molecules, or minerals produced by, consumed by, or otherwise attributed to the reaction between the β-lactam antibiotic hydrolyzing enzymes 122 and the β-lactamase substrate 128. For example, the solution characteristic can change as hydrogen ions ($H^+$) are produced as a result of the reaction between the β-lactam antibiotic hydrolyzing enzymes 122 and the β-lactamase substrate 128.

For example, the sensor 112 can be a pH sensor and exposing the pH sensor to the reaction mixture 212 in the reaction wells 204 can reveal a decrease in the pH of the reaction mixture 212 over time as the concentration of hydrogen ions ($H^+$) increases. In this case, the increase in the concentration of hydrogen ions ($H^+$) can be the result of the reaction between the β-lactam antibiotic hydrolyzing enzymes 122 released from the lysing of the bacteria 102 and the β-lactamase substrate 128 in the reaction wells 204. A decrease in the pH of such a reaction mixture 212 can indicate the presence of β-lactam antibiotic hydrolyzing bacteria 136 in the sample 104 originally introduced.

As shown in FIG. 2, the parameter analyzer 114 can be a standalone unit or meter coupled to the sensor 112. In other embodiments not shown in FIG. 2 but contemplated by this disclosure, the parameter analyzer 114 can be integrated with the well plate 202 or the sensors 112. The parameter analyzer 114, the sensor 112, or a combination thereof can detect the presence of the β-lactam antibiotic hydrolyzing bacteria 136 within a detection window 138.

In some embodiments, the detection window 138 can be between one minute and five minutes. In other embodiments, the detection window 138 can be between 60 minutes and 120 minutes. In yet additional embodiments, the detection window 138 can be between five minutes and 60 minutes. For example, the sensor 112 can monitor the solution characteristic of the solution in each of the reaction wells 204 between one minute and 120 minutes in order detect the presence of the β-lactam antibiotic hydrolyzing bacteria 136 in the sample 104 originally introduced.

The parameter analyzer 114 can also be connected to or communicatively coupled to a display 140 or display component configured to provide a result of the detection or a read-out of the electrical characteristic of the sensor 112. In certain embodiments, the parameter analyzer 114 can be a mobile device, a handheld device, a tablet device, or a computing device such as a laptop or desktop computer and the display 140 can be a mobile device display, a handheld device display, a tablet display, or a laptop or desktop monitor. In one embodiment, the parameter analyzer 114 can display a result indicating the presence of β-lactam antibiotic hydrolyzing bacteria 136 in the sample 104 via the display 140 of the parameter analyzer 114 in step 2F. In another embodiment, the parameter analyzer 114 can wirelessly communicate a result indicating the presence of β-lactam antibiotic hydrolyzing bacteria 136 in the sample 104 to a computing device having the display 140.

In one embodiment, the parameter analyzer 114 can be a voltage meter. In other embodiments, the parameter analyzer 114 can be, but is not limited to, a multimeter, a source meter, an ammeter, a capacitance analyzer, or a combination thereof.

The electrical characteristic of the sensor 112 can include, but is not limited to, a voltage, an impedance, a current, a capacitance, a resistance, a resonant frequency, a noise level, a level of induction, or a combination thereof of the sensor 112. For example, the electrical characteristic can be an internal voltage or current of the sensor 112. The change in the electrical characteristic can include, but is not limited to, a voltage change, an impedance change, a current change, a capacitance change, a resistance change, a change in resonant frequency, a noise level change, an induction change, or a combination thereof of the sensor 112.

One advantage of the system 200 shown in FIG. 2 is the ability to determine the resistance of the bacteria 102 in the sample 104 to multiple β-lactam antibiotics, inhibitors, or a combination thereof simultaneously. The steps depicted in FIG. 2 do not require the particular order shown to achieve the desired result. Moreover, certain steps or processes may be omitted or occur in parallel in order to achieve the desired result.

Figure 3:
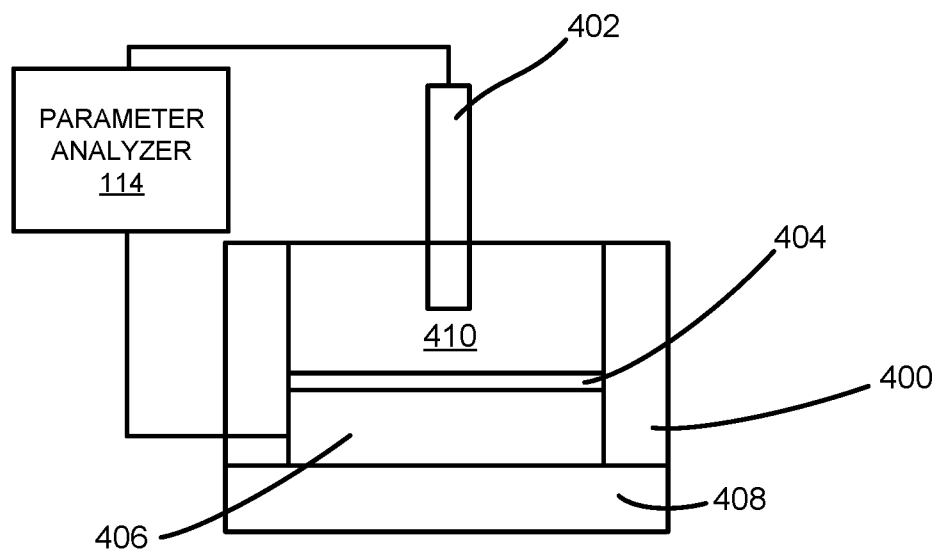
FIG. 3 illustrates a side view of an embodiment of a sensor of the system having an external reference electrode.

FIG. 3 illustrates a side cross-sectional view of one embodiment of the sensor 112. In this embodiment, the sensor 112 can include, but is not limited to, an electrochemical cell comprising container walls 400, an external reference electrode 402, a functionalization layer 404, a conductor layer 406, and a substrate layer 408. The sensor 112 can be configured to receive or be in fluid contact with a solution. For example, the sensor 112 can receive a solution and retain the solution within the container walls 400 as shown in FIG. 3. In other embodiments not shown in the figures but contemplated by this disclosure, one or more layers of the sensor 112 can be in fluid contact with the solution even though the solution is not retained within the container walls 400 of the sensor 112 or the sensor 112 has no container walls 400.

In all such embodiments, the solution can be any of the reaction mixture 126 or the reaction mixture 212. For purposes of FIGS. 3, 4, 5A, 5B, the reaction mixture 126 or the reaction mixture 212 can be referred to as electrolyte 410 when such a solution is either retained by the container walls 400 of the sensor 112 or in fluid communication or contact with one or more electrodes or layers of the sensor 112.

The sensor 112 can be connected or coupled to the parameter analyzer 114. In one embodiment, the parameter analyzer 114 can be coupled to both the external reference electrode 402 and the conductor layer 406. In other embodiments, the parameter analyzer 114 can be coupled to the external reference electrode 402, the conductor layer 406, as well as other layers.

As shown in FIG. 3, the external reference electrode 402 can extend into the electrolyte 410. In one embodiment, the electrolyte 410 can be any of the reaction mixture 126 or the reaction mixture 212. The electrolyte 410 can comprise portions of the sample 104. The electrolyte 410 can also comprise, but is not limited to, a buffered solution, a nutrient solution, or liquid culture media.

When the parameter analyzer 114 is coupled to the external reference electrode 402, the conductor layer 406, or another layer, the parameter analyzer 114 can measure a difference in the electrical characteristic of the 112. The external reference electrode 402 can have a stable and well-known internal reference potential and can also act as a differential noise filter for removing electrical noise from measurements taken by the sensor. An operator or clinician can use this setup to determine or record a relative change in the electrical characteristic of the sensor 112 rather than having to ascertain an absolute change. An operator or clinician can also use the external reference electrode 402 to determine or record a relative difference between the electrical characteristics of multiple sensors 112. In one embodiment, the external reference electrode 402 can be a stand-alone probe or electrode. In other embodiments, the external reference electrode 402 can be coupled to the parameter analyzer 114 or a reader connected to the parameter analyzer 114. The parameter analyzer 114 can also be used to apply a voltage to the external reference electrode 402.

In one embodiment, the external reference electrode 402 can be a silver/silver chloride (Ag/AgCl) electrode. In other embodiments, the external reference electrode 402 can be, but is not limited to, a saturated calomel reference electrode (SCE) or a copper-copper (II) sulfate electrode (CSE).

The substrate layer 406 can be composed of, but is not limited to, any non-conducting material such as a polymer, an oxide, a ceramic, or a composite thereof. As depicted in FIG. 3, the conductor layer 406 can be disposed on or cover the substrate layer 408.

The conductor layer 406 can be composed of, but is not limited to, a metal, a semiconducting material, a metal/metal-salt, or a combination thereof. For example, the conductor layer 406 can be composed of, but is not limited to, silicon, gold, silver, aluminum, platinum, or a composite thereof. The conductor layer 406 can also be an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof. The conductor layer 406 can be composed of any conducting material which allows an electrical property change to be measured, including, but not limited to, a voltage change, a capacitance change, a conductance change, and/or a current change measured through the conductor layer 406, the functionalization layer 404, and the electrolyte 410 to the external reference electrode 402.

As depicted in FIG. 3, the functionalization layer 404 can be disposed on or cover the conductor layer 406. The functionalization layer 404 can comprise silanes, DNA, proteins, antibodies, self-assembled mono layers (SAMs), oxides, buffered hydrogels, PVC, parylene, polyACE, or any other biochemically active materials. The functionalization layer 404 can be configured to facilitate the sensor 112 from interacting with ions, analytes, or other molecules or byproducts in the electrolyte 410. For example, the functionalization layer 404 can be a pH-sensitive layer.

In one example, the functionalization layer 404 can comprise hydroxyl groups which can interact with hydrogen ions ($H^+$) in the electrolyte 410. This interaction can generate a change in the electrical characteristic between the sensor 112 and the external reference electrode 402 as detected by the parameter analyzer 114. In one embodiment, this interaction can create a measurable change in the electrical characteristic of the sensor 112 at the interface between the electrolyte 410/functionalization layer 404 or the interface between the electrolyte 410/conductor layer 406.

For example, the parameter analyzer 114 can be a voltmeter and the voltmeter can detect a voltage (potential) change ($\Delta V$) at or near the functionalization layer 404 exposed to the electrolyte 410. The voltage change can be determined with respect to the external reference electrode 402 extending into or in contact with the electrolyte 410. In this embodiment, the functionalization layer 404 and the conductor layer 406 can be considered part of a working or active electrode.

As depicted in FIG. 3, the electrolyte 410, the functionalization layer 404, and the conductor layer 406 can be surrounded by the container walls 400. The container walls 400 can be made of an inert or non-conductive material. The container walls 400 can comprise, but is not limited to, a polymeric material such as polyvinyl chloride (PVC), poly (methyl methacrylate) (PMMA), polydimethylsiloxane (PDMS), a ceramic, glass, or a combination thereof.

Figure 4:
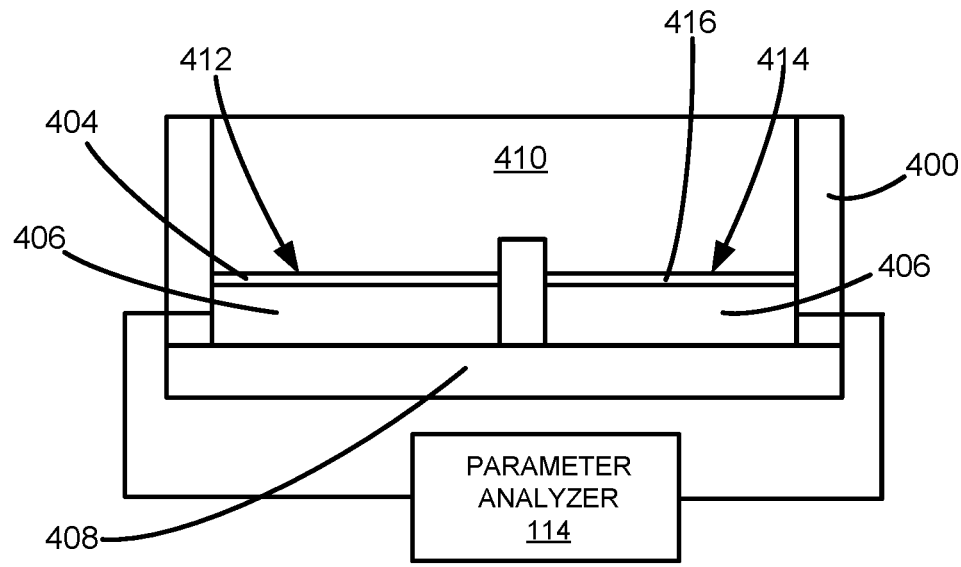
FIG. 4 illustrates a side view of an embodiment of a sensor of the system having an on-chip reference electrode.

FIG. 4 illustrates a side cross-sectional view of another embodiment of the sensor 112. In this embodiment, the sensor 112 comprises a working electrode 412 and an on-chip reference electrode 414. In this embodiment, the working electrode 412 (i.e., the active electrode) and the on-chip reference electrode 414 can be disposed on the same substrate layer 408. The substrate layer 408 can be composed of the same material as the substrate layer 408 depicted in FIG. 3.

The electrolyte 410 can flow over or be exposed to both the working electrode 412 and the on-chip reference electrode 414 simultaneously. In this embodiment, the working electrode 412 and the on-chip reference electrode 414 can be separated by a container wall 400 or container divide.

The working electrode 412 can comprise the functionalization layer 404 disposed on or covering the conductor layer 406. The functionalization layer 404 can comprise silanes, DNA, proteins, hydroxyl group, antibodies, oxides, self-assembled mono layers (SAMs), buffered hydrogels, PVC, parylene, polyACE, or any other biochemically active materials.

As shown in FIG. 4, a passivation layer 416 can be disposed on or cover the conductor layer 406. The passivation layer 416 can be configured to prevent the on-chip reference electrode 414 from interacting with analytes, ions, or other molecules or byproducts in the electrolyte 410. For example, the passivation layer 416 can be a pH-insensitive layer. The passivation layer 416 can comprise silanes, self-assembled monolayers (SAMs), buffered hydrogels, parylene, polyACE, or any other biochemically inert material.

In this embodiment, the parameter analyzer 114 can have a lead connection wire, such as a copper wire, connected to the conductor layer 406 of the working electrode 412 and another lead connection wire connected to the conductor layer 406 of the on-chip reference electrode 414.

In this and other embodiments, the sensor 112 shown in FIG. 4 miniaturizes the sensor set-up shown in FIG. 3. The on-chip reference electrode 414 obviates the need for an external reference electrode, such as the external reference electrode 402. The on-chip reference electrode 414 can also be a silver/silver chloride (Ag/AgCl) electrode. In other embodiments, the on-chip reference electrode 414 can be, but is not limited to, a saturated calomel reference electrode (SCE) or a copper-copper (II) sulfate electrode (CSE). The on-chip reference electrode 414 provides similar functionality as that of the external reference electrode 402 in this embodiment of the sensor 112. The passivation layer 416 of the on-chip reference electrode 414 prevents the conductor layer 406 covered by the passivation layer 416 from interacting with the ions, analytes, or other molecules or byproducts in the electrolyte 410. This allows a reader or another device from being able to differentiate the electrical signals obtained by the parameter analyzer 114. In other embodiments, the on-chip reference electrode 414 can be without a passivation layer 416.

In one embodiment where the conductor layer 406 is used as a reference electrode, the conductor layer 406 can be a metal covered with a metal salt such as a metal chloride. In another embodiment, the conductor layer 406 can also be covered with an oxide. For example, the conductor layer 406 can be a silver/silver chloride contact. In this embodiment, the conductor layer 406 can be covered by, but is not limited to, a passivation layer 416 such as a KCL electrolyte gel or KCL solution, to prevent the conductor layer 406 from interacting with analytes, ions, or other molecules or byproducts in the electrolyte 410 and to act as a reference electrode.

Figure 5A:
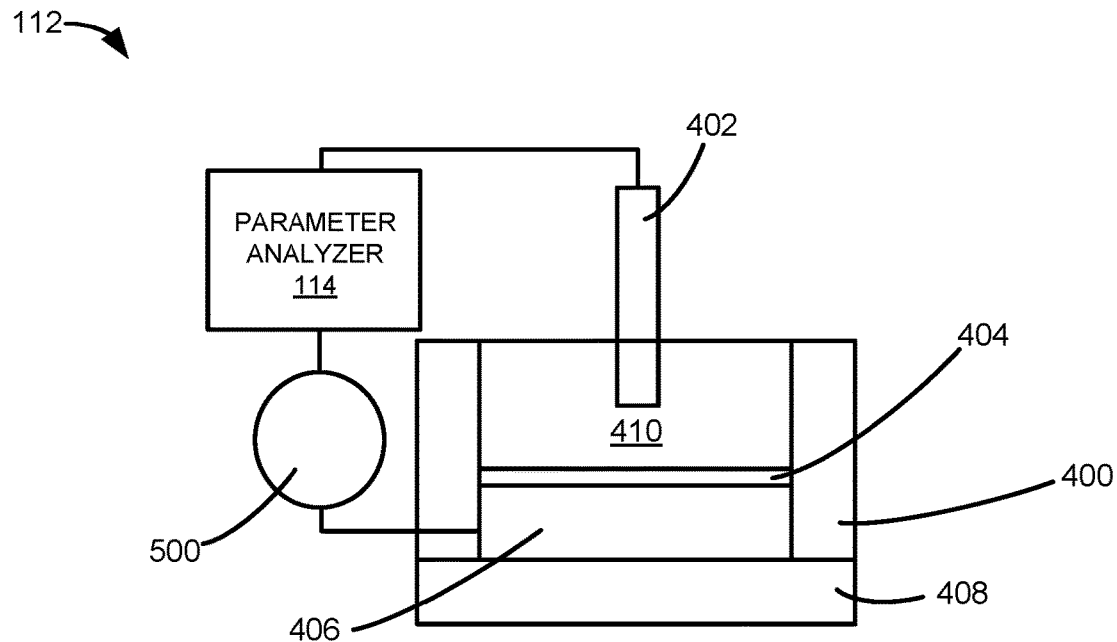
FIG. 5A illustrates a side view of an embodiment of a sensor of the system having an external reference electrode and a power source.

FIG. 5A illustrates a side cross-sectional view of an embodiment of the sensor 112 of FIG. 3 having a power source 500. The power source 500 can apply a DC or AC voltage (usually in the range of +/−5V) between the conductor layer 406 and the external reference electrode via the functionalization layer 404 and the electrolyte 410. This voltage can also be set to be used as a working point.

Depending on the concentration or amount of analytes, ions, molecules, or cellular byproducts present in the electrolyte 410, a change in the electrical characteristic (e.g., a shift ($\Delta V$) of the voltage measurement curve) will occur as the analytes, ions, molecules, or cellular byproducts interact with the sensor 112. This change can be measured by the parameter analyzer 114. In one embodiment, when a voltage is applied over time or when different electrolyte 410 solutions are introduced to the sensor 112, the analytes, ions, molecules, or cellular byproducts can interact with the functionalization layer 404, causing an additional electrical characteristic change, which can also be detected by the parameter analyzer 114.

Figure 5B:
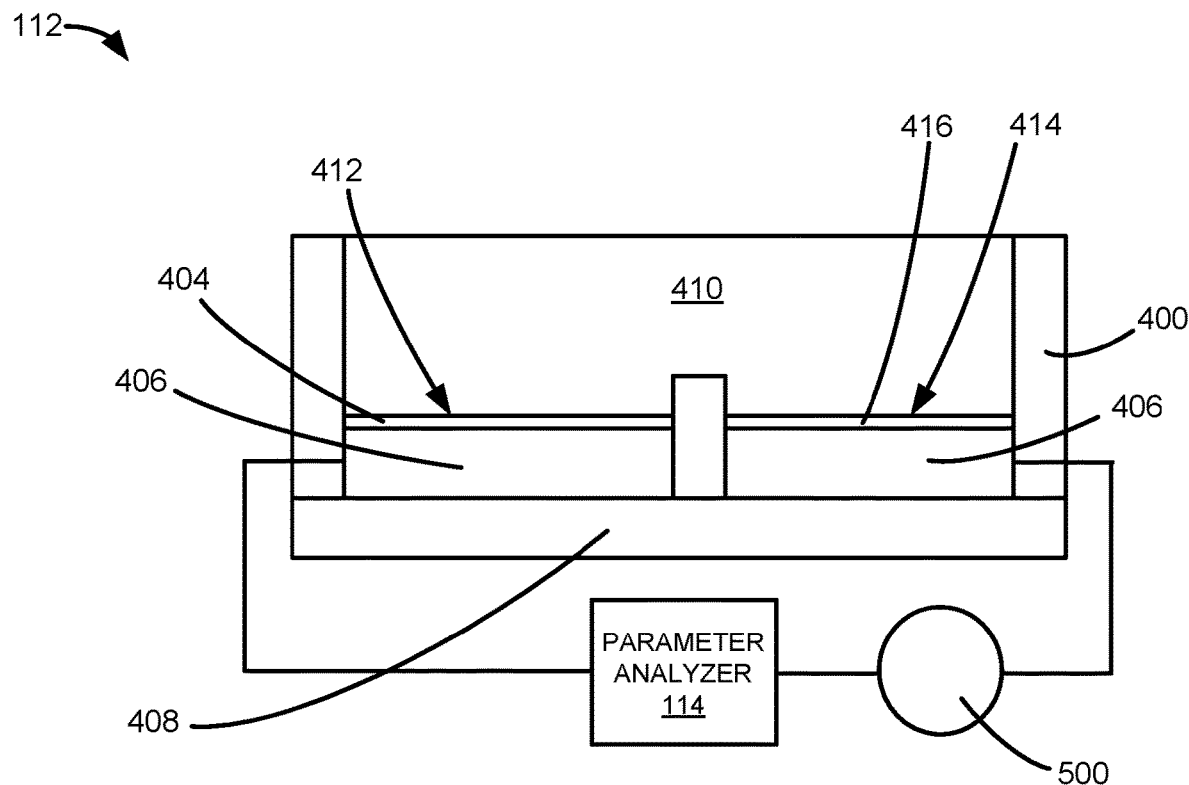
FIG. 5B illustrates a side view of an embodiment of a sensor of the system having an on-chip reference electrode and a power source.

FIG. 5B illustrates a side cross-sectional view of an embodiment of the sensor 112 of FIG. 4 having a power source 500. The power source 500 can apply a DC or AC voltage (usually in the range of +/−5V) between the conductor layer 406 of the working electrode 412 (i.e., the active electrode), through the electrolyte 410 and the conductor layer 406 of the on-chip reference electrode 414. This voltage can also be set to be used as a working point. Depending on the concentration or amount of analytes, ions, molecules, or cellular byproducts present in the electrolyte 410, a change in the electrical characteristic, e.g. a shift ($\Delta V$) of the voltage measurement curve, can occur, as the analytes, ions, molecules, or cellular byproducts interact with the sensor 112. This change can be measured by the parameter analyzer 114. In one configuration, when a voltage is applied over time or when different electrolytes 410 are introduced to the sensor 112, the analytes, ions, molecules, or cellular byproducts can interact with the functionalization layer 404, causing an additional electrical characteristic change that can be detected by the parameter analyzer 114.

In another embodiment, a potential or a current can be applied between the working electrode 412 through the electrolyte 410 to the on-chip reference electrode 414. The parameter analyzer 114 can then record a current, which flows between the two electrodes. Depending on the concentration or amount of analytes, ions, chemicals, molecules, or cellular byproducts present in the electrolyte 410, a change of the electrical characteristics (in this case, a shifting of the current measurement curve ($\Delta I$)) can occur, as the analytes, ions, molecules, or cellular byproducts interact with the electrolyte 410 or the sensor 112.

Figure 6A:
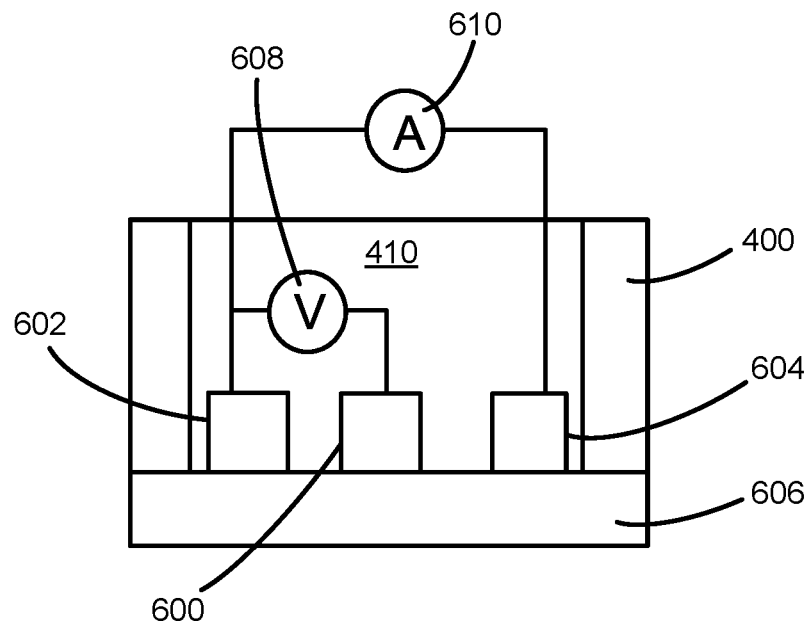
FIG. 6A illustrates a side view of an embodiment of a sensor of the system.

FIG. 6A illustrates a side cross-sectional view of another embodiment of the sensor 112. In this embodiment, the sensor 112 can be an electrochemical sensing device. In this embodiment, the sensor 112 comprises a working electrode 600, a reference electrode 602, and a counter electrode 604. The working electrode 600, the reference electrode 602, and the counter electrode 604 can be disposed on the same substrate layer 606. The substrate layer 606 can be composed of, but is not limited to, any non-conducting material such as a polymer, an oxide, a ceramic, or a composite thereof. For example, the substrate layer 606 can be composed of the same material as the substrate layer 408 depicted in FIG. 3.

The electrolyte 410 can flow over or be exposed to the working electrode 600, the reference electrode 602, and the counter electrode 604 simultaneously. As depicted in FIG. 6A, the electrolyte 410 can be surrounded by the container wall 400. The container wall 400 can be made of an inert or non-conductive material. The container wall 400 can hold or retain the electrolyte 410.

The sensor 112 can be connected to a voltmeter 608 and an ammeter 610 or any other meter or measurement device. The voltmeter 608 can have one lead connection wire, such as a copper wire, connected to the working electrode 600 and another lead connection wire connected to the reference electrode 602. The ammeter 610 can also have one lead connection wire connected to the reference electrode 602 and another lead connection wire connected to the counter electrode 604.

Figure 6B:
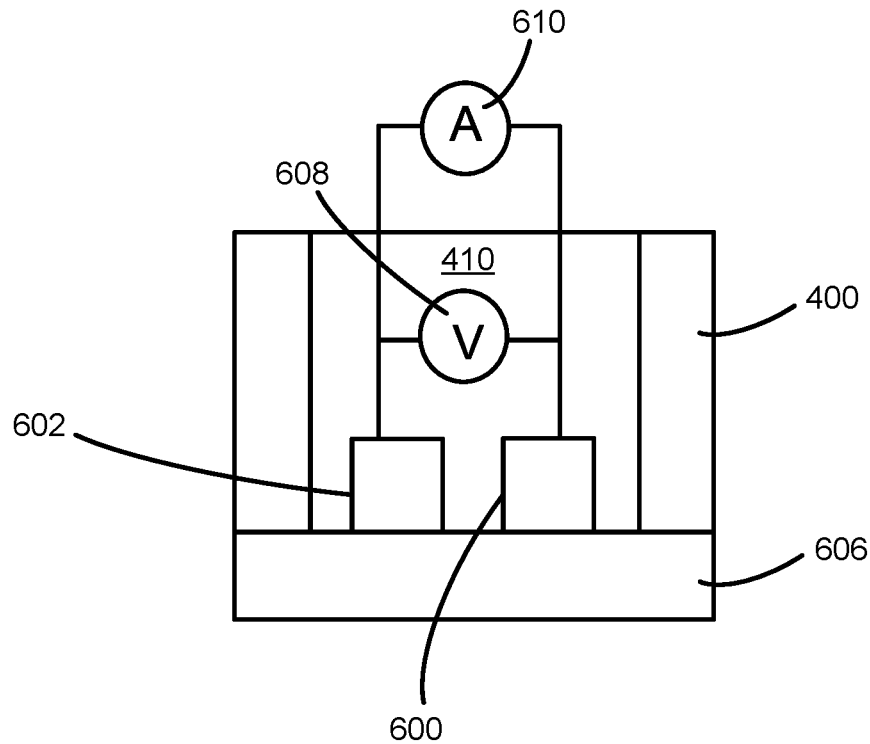
FIG. 6B illustrates a side view of another embodiment of a sensor of the system.

FIG. 6B illustrates a side cross-sectional view of another embodiment of the sensor 112. The sensor 112 of FIG. 6B can be a two electrode setup where the reference electrode 602 can also act as a counter electrode. In this embodiment, a voltage can be applied between the reference electrode 602 and the working electrode 600. At the same time, the current flowing from the reference electrode 602 though the electrolyte 410 to the working electrode 600 can be measured. To detect a given analyte, molecule, or ion, a known chemical or solution can be added to the electrolyte 410. This chemical can react with the target analytes, ions, molecules or cellular byproducts, and alter a current or voltage curve. Additional chemicals can also be added to generate an electrical current that can be measured by the system.

Figure 7:
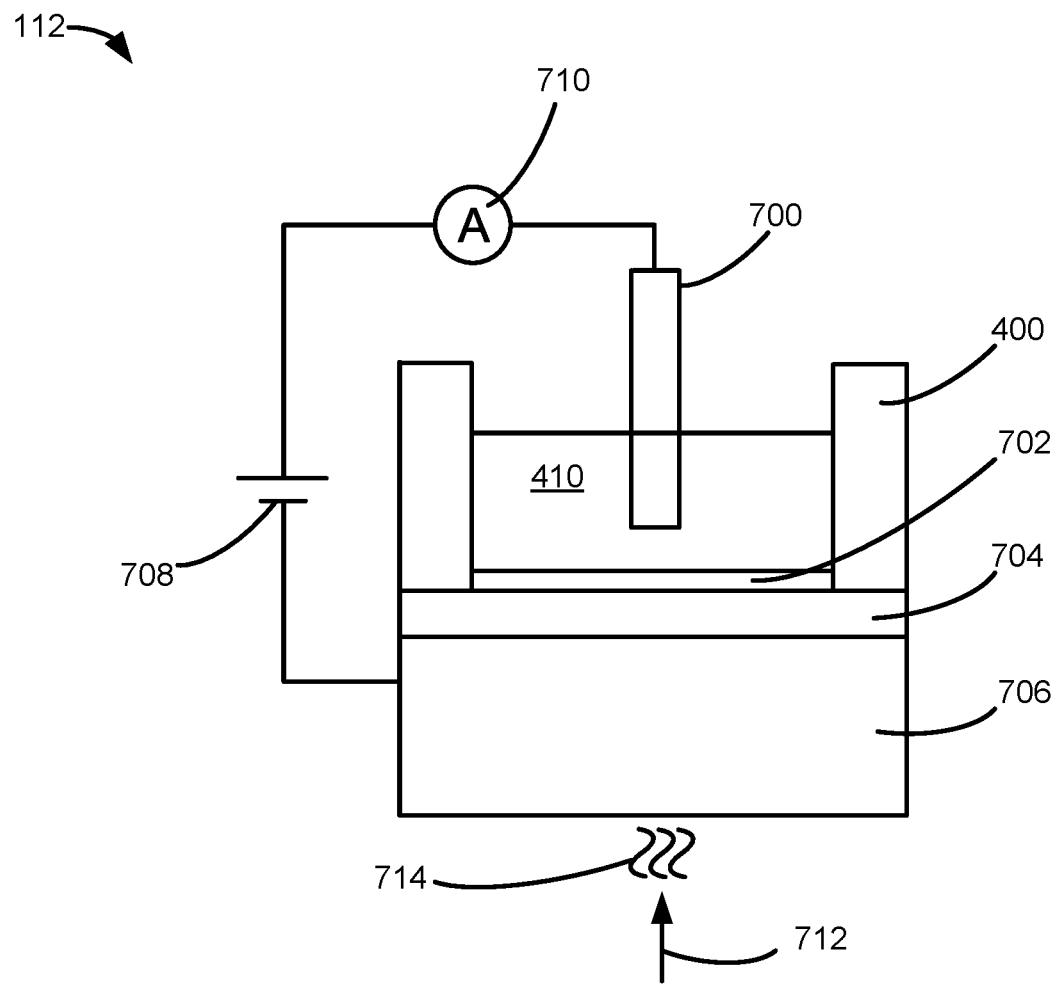
FIG. 7 illustrates a side view of an embodiment of a light-addressable potentiometric (LAP) sensor of the system.

FIG. 7 illustrates a side cross-sectional view of another embodiment of the sensor 112. In one embodiment, the sensor 112 can be a photocurrent sensor such as a light-addressable potentiometric (LAP) sensor. The sensor 112 can comprise an external reference electrode 700, an electrolyte 410 or electrically conducting solution retained by container walls 400, a functionalization layer 702, an insulator layer 704, and a semiconductor layer 706. The sensor 112 can be connected or coupled to a voltage source 708 and an ammeter 710. The voltage source 708 can be connected in series with the ammeter 710, for example, with one lead connection wire connected to the semiconductor layer 706 and the other lead connection wire connected to the external reference electrode 700.

As depicted in FIG. 7, the electrolyte 410 and the functionalization layer 702 can be surrounded by a container wall 400. The container wall 400 can be made of an inert or non-conductive material. The container wall 400 can hold or retain the electrolyte 410. As shown in FIG. 7, the external reference electrode 700 can extend into the electrolyte 410.

The voltage source 708 can apply a known potential to the sensor 112 through the external reference electrode 700. This voltage can be, but is not limited to, a DC or AC voltage. In one embodiment, the external reference electrode 700 can be, but is not limited to, a silver/silver chloride (Ag/AgCl) electrode. In other embodiments, the external reference electrode 700 can be a saturated calomel reference electrode (SCE) or a copper-copper (II) sulfate electrode (CSE).

The sensor 112 can comprise the insulator layer 704 disposed on or covering the semiconductor layer 706. The semiconductor layer 706 can be a layer of doped semiconducting material. The semiconductor layer 706 can be composed of, but is not limited to, a layer of doped silicon. The semiconductor layer 706 can also be made of an organic semiconductor, a carbon nanotube, graphene, an organic conductor such as those derived from polyacetylene, polyaniline, Quinacridone, Poly(3,4-ethylenedioxythiophene) or PEDOT, PEDOT: polystyrene sulfonate (PSS), or a combination thereof.

The insulator layer 704 (which can also be referred to as an isolator layer) can be a high-k dielectric layer or a material layer having a high dielectric constant (k). For example, the insulator layer 704 can comprise aluminum oxide, hafnium oxide, titanium oxide, zirconium oxide, yttrium oxide, tantalum oxide, hafnium silicate, zirconium silicate, silicon nitride, aluminum nitride, hafnium nitride, zirconium nitride, or a combination thereof. As a more specific example, the insulator layer 704 can comprise aluminum dioxide, hafnium dioxide, zirconium dioxide, or a combination thereof. In other embodiments, the insulator layer 216 can comprise a silicon dioxide layer.

As depicted in FIG. 7, the functionalization layer 702 can be disposed on or cover the insulator layer 704. The functionalization layer 702 can comprise silanes, DNA, proteins, antibodies, self-assembled mono layers (SAMs), buffered hydrogels, PVC, parylene, polyACE, or any other biochemically active materials. The functionalization layer 702 can be configured to facilitate the sensor 112 from interacting with ions, analytes, or other molecules or byproducts in the electrolyte 410. For example, the functionalization layer 702 can be a pH-sensitive layer. In one example, the functionalization layer 702 can comprise hydroxyl groups which can interact with hydrogen ions ($H^+$) in the electrolyte 410. In another embodiment, an insulator layer 704 made of an oxide can be used as the functionalization layer 702.

An external DC bias voltage can be applied. When a light source 712 (e.g., a modulated light pointer or source) illuminates the bulk silicon, light induced charge carriers can be separated by an internal electric field and a photocurrent can be detected by a peripheral circuit. The amplitude of the photocurrent can depend on the local surface potential.

The light source 712 can direct light 714 of specific wavelengths at the doped semiconductor layer 706. When the semiconducting material, such as silicon, in the semiconductor layer 706 absorbs light 714 matching its excitation frequency, electron-hole pairs are generated in the bulk of the semiconductor layer 706 and electrons move to the interface between the semiconductor layer 706 and the insulator layer 704 or the functionalization layer 702. As a result, a transient photocurrent can be detected by the ammeter 710. The light source 712 can modulate the wavelengths of the light 714 directed at the semiconductor layer 706 in order to induce an alternating current (AC) photocurrent.

The voltage source 708 can apply a bias voltage to the electrolyte 410 via the external reference electrode 700. This bias voltage can be applied between the semiconductor layer 706 and the reference electrode 700. The bias voltage can be set so as to repel electrons from the doped semiconductor layer 706 to form a depletion layer. The bias voltage can be set so as to repel the electrons moving to the interface between the semiconductor layer 706 and the insulator layer 704 due to the light 714 directed at the semiconductor layer 706. At a low enough bias voltage, the depletion layer is not formed. At a large enough bias voltage, the photocurrent increases until reaching a limiting value.

A bias voltage is needed to form the depletion layer. The depletion layer can, in turn, assist in the generation of a photocurrent. In the embodiment depicted in FIG. 7, the light intensity of the light source 712 is fixed so the amplitude of the photocurrent depends on the bias voltage applied. In addition, sensing the amplitude of the photocurrent depends on the local surface potential. This potential is coupled to the bias voltage applied to the sensor 112. For example, a larger concentration of $H^+$ ions provides a larger value of this potential difference, causing the I-V curve to shift along the bias voltage axis. When the bias voltage is kept constant, a change in the photocurrent can indicated a change in the pH of the electrolyte 410.

Since the bias voltage is in series with the potential at the interface between the functionalization layer 702 and the electrolyte 410, a change in the solution characteristic of the electrolyte 410 (such as a change in analyte concentration or pH change) can change the bias voltage needed to maintain the constant photocurrent detected by the ammeter 710. For example, hydrogen ions in the solution can interact with the hydroxyl groups of the functionalization layer 702 and generate an additional potential change at the interface. This additional voltage will also cause a shift in the photocurrent, comparable to increasing or decreasing the bias voltage. In addition, hydrogen ions in the solution can also interact with the insulator layer 704 to generate a potential change at the interface and cause a shift in the photocurrent.

As shown in FIG. 7, the light source 712 can be focused so as to direct light 714 of a specific wavelength at a specific portion of the semiconductor layer 706. Moreover, a different light source or the same light source 712 can direct light 714 of a different wavelength at a different portion of the semiconductor layer 706. This allows facile multiplexing by creating a series of different sensing areas on one photocurrent sensor such that different areas of the sensor can be allocated for or dedicated to a different analyte, ion, or molecule.

Figure 8A:
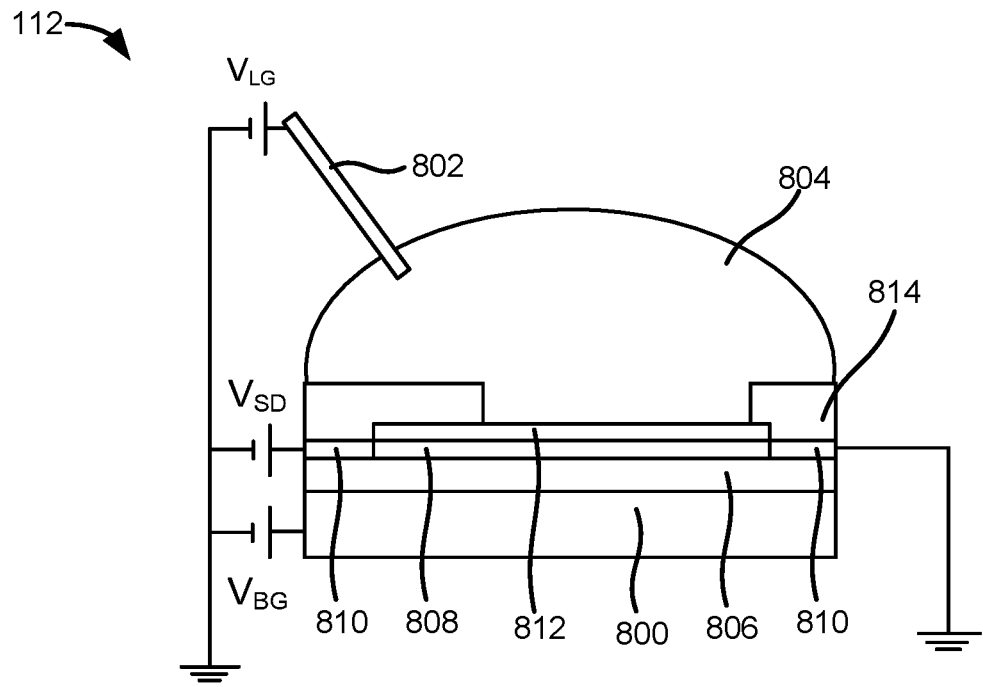
FIG. 8A illustrates a side view of another embodiment of a sensor of the system having an external reference electrode.

FIG. 8A illustrates a side view of another embodiment of the sensor 112 as an ion-sensitive field-effect transistor (ISFET). In this embodiment, the sensor 112 can be disposed on a semiconductor layer 800. The sensor 112 can have an external reference electrode 802 extending into a reaction mixture 804 in contact with the sensor 112. The reaction mixture 804 can include or refer to any of the reaction mixture 126 or the reaction mixture 212.

As depicted in FIG. 8A, the sensor 112 can comprise a semiconductor layer 800 and a base dielectric layer 806. The sensor 112 can comprise, but is not limited to, a polymer layer, a metal layer, a metalloid layer, a ceramic layer, an organic semiconductor, a carbon nanotube layer, a graphene layer, an organic conductor such as those derived from polyacetylene, polyaniline, Quinacridone, Poly(3,4-ethylenedioxythiophene) or PEDOT, PEDOT: polystyrene sulfonate (PSS), or a combination thereof. The semiconductor layer 800 can be composed of or comprise silicon or an oxide of silicon, which allows a voltage to be applied through the semiconductor layer 800 to the sensor channel 808.

The base dielectric layer 806 can be coupled or can be disposed on the semiconductor layer 800 to electrically insulate or isolate different sensors 112 from one another. In one embodiment, the base dielectric layer 806 can be composed of an oxide material. In other embodiments, the base dielectric layer 806 can be composed of any other material capable of providing insulation.

In one or more embodiments, the sensors 112 can be fabricated using a complementary metal oxide semiconductor (CMOS) process or a similar or different process. For example, the sensor 112 can be integrated CMOS ISFET sensors fabricated from p-type and n-type metal oxide semiconductor field-effect transistors (MOSFETs). In another embodiment, the sensor 112 can be organic field-effect transistors (OFETs).

As depicted in FIG. 8A, the sensor 112 can comprise sensor contacts 810, a sensor channel 808 in between the sensor contacts 810, a gate dielectric layer 812 coupled to or on top of the sensor channel 808, and an encapsulating layer 814 partially covering the gate dielectric layer 812 of the sensor 112. The sensor contacts 810 can include a source contact and a drain contact. For example, the sensor contacts 810 can be composed of highly doped p-type material. The sensor channel 808 can act as a bridge between the two sensor contacts 810 and can be composed of any electrically conductive material or coating that allows for electrical communication between the sensor contacts 810.

The gate dielectric layer 812 can be coupled to or disposed on top of the sensor channel 808. In certain embodiments, the gate dielectric layer 812 can be a high-k dielectric layer or a material layer having a high dielectric constant (k). For example, the gate dielectric layer 812 can comprise aluminum oxide, hafnium oxide, titanium oxide, zirconium oxide, yttrium oxide, tantalum oxide, hafnium silicate, zirconium silicate, silicon nitride, aluminum nitride, hafnium nitride, zirconium nitride, or a combination thereof. As a more specific example, the gate dielectric layer 812 can comprise aluminum dioxide, hafnium dioxide, zirconium dioxide, or a combination thereof. In other embodiments, the gate dielectric layer 812 can comprise a silicon dioxide layer.

The sensor 112 can be partially covered by the encapsulating layer 814. The encapsulating layer 814 can be composed of any inert or non-conductive material for protecting the sensor 112 from being exposed to solutes or contaminants in the reaction mixture 804 or parasitic currents that would damage or degrade the sensor 112.

As depicted in FIG. 8A, the sensor 112 can also comprise an external reference electrode 802 in liquid communication with the reaction mixture 804 and the sensor 112. The reaction mixture 804 can be introduced to the sensor 112 from the filter housing 108, the reaction wells 204, the fluid delivery conduit 106, the multichannel delivery device 206, or any other fluid delivery device. The reaction mixture 804 can cover the sensor 112 when introduced to the sensor 112. In other embodiments, the reaction mixture 804 can partially cover or be in liquid communication with the sensor 112 when introduced to the sensor 112.

The external reference electrode 802 can apply a potential, such as a liquid gate potential, to the reaction mixture 804. In one embodiment, the external reference electrode 802 can be a standalone probe or electrode. In other embodiments, the external reference electrode 802 can be coupled to the parameter analyzer 114. The external reference electrode 802 can have a stable and well-known internal voltage and can act as a differential noise filter for removing electrical noise from measurements taken by the sensor 112.

In one embodiment, the external reference electrode 802 can be, but is not limited to, a silver/silver chloride (Ag/AgCl) electrode. In other embodiments, the external reference electrode 802 can be a saturated calomel reference electrode (SCE) or a copper-copper (II) sulfate electrode (CSE).

The external reference electrode 802 can be used to determine or record a relative change in the electrical characteristic of the sensor 112 rather than having to ascertain an absolute change. The external reference electrode 802 can also be used to determine or record a relative difference between the electrical characteristics of different sensors 112.

A back-gate voltage Vbg can be applied via the silicon substrate. The electrical characterization of ISFETs can be performed by applying a source-drain voltage Vsd to measure the source-drain current Isd. In another embodiment, a liquid gate voltage can be applied to a solution via a reference electrode. The electrical characterization of ISFETs can be performed applying a source-drain voltage Vsd to measure the source-drain current Isd. In another embodiment, a dual-gate approach can be used by applying gate voltages simultaneously to the back gate and to the liquid gate. This allows an operator to tune the device to different working positions, optimizing the sensitivity. The back-gate voltage Vbg is applied to the Si substrate, while the liquid gate voltage Vlg is applied via a reference electrode. At the same time, the liquid potential Vlg can be measured by the reference electrode. When the ion concentration in the solution is changing, the ISFET responds with a change in the electrical characteristic. For example, in case of proton (H+) changes, the protons interact with the oxide surface of the ISFET. This is the expected dependence for an oxide surface exposing hydroxl (−OH) groups to the liquid. The change in surface charge density caused by a pH change is described by the site-binding model, which takes into account that −OH groups can be protonated or deprotonated. This model predicts an approximate linear relation between the surface charge density and the proton concentration. Since the surface charge acts as an additional gate, the ISFET is responding to the additional gate effect.

Figure 8B:
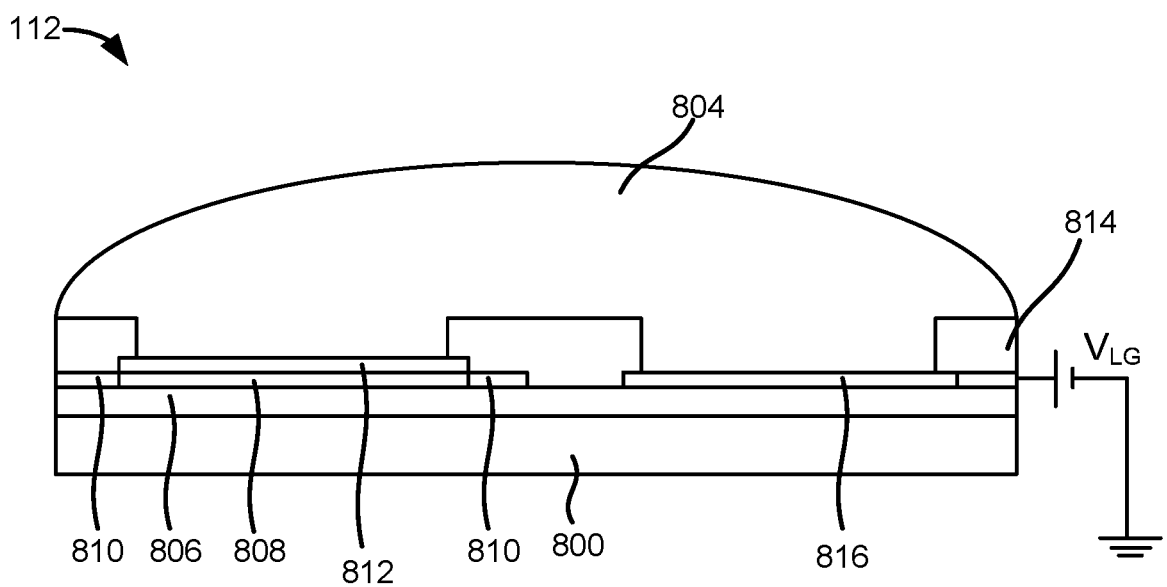
FIG. 8B illustrates a side view of another embodiment of a sensor of the system having an on-chip reference electrode.

FIG. 8B illustrates a side view of another embodiment of the sensor 112 comprising an on-chip reference electrode 816. The on-chip reference electrode 816 can serve the same purpose as the external reference electrode 802 except fabricated as a miniaturized version thereof or as a chip or sensor on the semiconductor layer 800 or the base dielectric layer 806. The on-chip reference electrode 816 can also be partially covered by the encapsulating layer 814. The on-chip reference electrode 816 can apply a liquid gate voltage ($V_{LG}$) to the reaction mixture 804.

The on-chip reference electrode 816, the external reference electrode 802, or a combination thereof can be comprised of a metal, a semiconductor material, or a combination thereof. In one embodiment, a control sensor can act as the on-chip reference electrode 816. The metal of the on-chip reference electrode 816 can be covered by, but is not limited to, an oxide layer, a silane layer, or a combination thereof.

The on-chip reference electrode 816 can be a transistor with very similar electrical properties as compared to the sensor 112 but with a passivated surface such as a reference FET (RFET) (which is contemplated by this disclosure but is not shown in the figures). The RFET can be an ISFET with a pH-passivating membrane, ion-blocking layers of photoresist material, or other polymers. The on-chip reference electrode 816 can comprise one or more pH-insensitive layers covering an ISFET. Such pH-insensitive layers can include silanes, self-assembled mono layers (SAMs), buffered hydrogels, PVC, parylene, polyACE, or any other chemically inert material. Also a metal, such as Au, Ag or Pt, can be used as a quasi-reference electrode evaporated on the substrate carrier. In another embodiment, the on-chip reference electrode 816 can be a metal combined with a metal salt such as an Ag/AgCl reference electrode.

FIG. 9A illustrates a side view of another embodiment of the sensor 112 comprising an active sensor 900, a control sensor 902, and an external reference electrode 802. FIG. 9A illustrates the semiconductor layer 800 having the active sensor 900 and the control sensor 902 disposed on it and the external reference electrode 802 extending into the reaction mixture 804 in fluid contact or communication with (or exposed to) the active sensor 900 and the control sensor 902. Similar to the sensor 112 depicted in FIGS. 8A and 8B, the active sensor 900 and the control sensor 902 can comprise a pair of sensor contacts 810, a sensor channel 808 in between the sensor contacts 810, a gate dielectric layer 812 coupled to or on top of the sensor channel 808, and an encapsulating layer 814 partially covering the gate dielectric layer 812 of the control sensor 902.

The sensor contacts 810 can include a source contact and a drain contact. The sensor channel 808 can act as a bridge between the two sensor contacts 810 and can be composed of any electrically conductive material or coating that allows for electrical communication between the sensor contacts 810.

The gate dielectric layer 812 can be coupled to or disposed on top of the sensor channel 808. In certain embodiments, the gate dielectric layer 812 can be a high-k dielectric layer or a material layer having a high dielectric constant. For example, the gate dielectric layer 812 of the control sensor 902 can comprise aluminum oxide, hafnium oxide, titanium oxide, zirconium oxide, yttrium oxide, tantalum oxide, hafnium silicate, zirconium silicate, or a combination thereof. As a more specific example, the gate dielectric layer 812 can comprise aluminum dioxide, hafnium dioxide, zirconium dioxide, or a combination thereof. In other embodiments, the gate dielectric layer 812 can comprise a silicon dioxide layer.

The encapsulating layer 814 can be composed of any inert or non-conductive material for protecting the control sensor 902 from being exposed to solutes or contaminants in the reaction mixture 804 that would damage or degrade the control sensor 902.

In the example embodiment shown in FIG. 9A, the control sensor 902 can comprise a passivation layer 904 coupled to or disposed on the gate dielectric layer 812. The passivation layer 904 can be composed of, but is not limited to, a polymer layer, a metallic layer, a self-assembled monolayer (SAM), or a combination thereof. The passivation layer 904 can be used to prevent binding of ions or molecules to the surface of the control sensor 902. In other embodiments, the control sensor 902 can be without the passivation layer 904 and the makeup of the control sensor 902 can be identical to the active sensor 900. For example, the passivation layer 904 can be a pH-passivating membrane, an ion-blocking layer, a photoresist material, or any other polymer. In addition, the passivation layer 904 can be a pH-insensitive layer covering an ISFET. Examples of pH-insensitive layers include silanes, SAMs, buffered hydrogels, PVC, parylene, polyACE, or a combination thereof.

FIG. 9B illustrates a side view of another embodiment of the sensor 112 having the active sensor 900, the control sensor 902, and the on-chip electrode 816 disposed on it, which can be used to apply a voltage to the solution. As shown in FIG. 9B, the on-chip electrode 816 can be disposed or located in between the active sensor 900 and the control sensor 902.

Figure 10A:
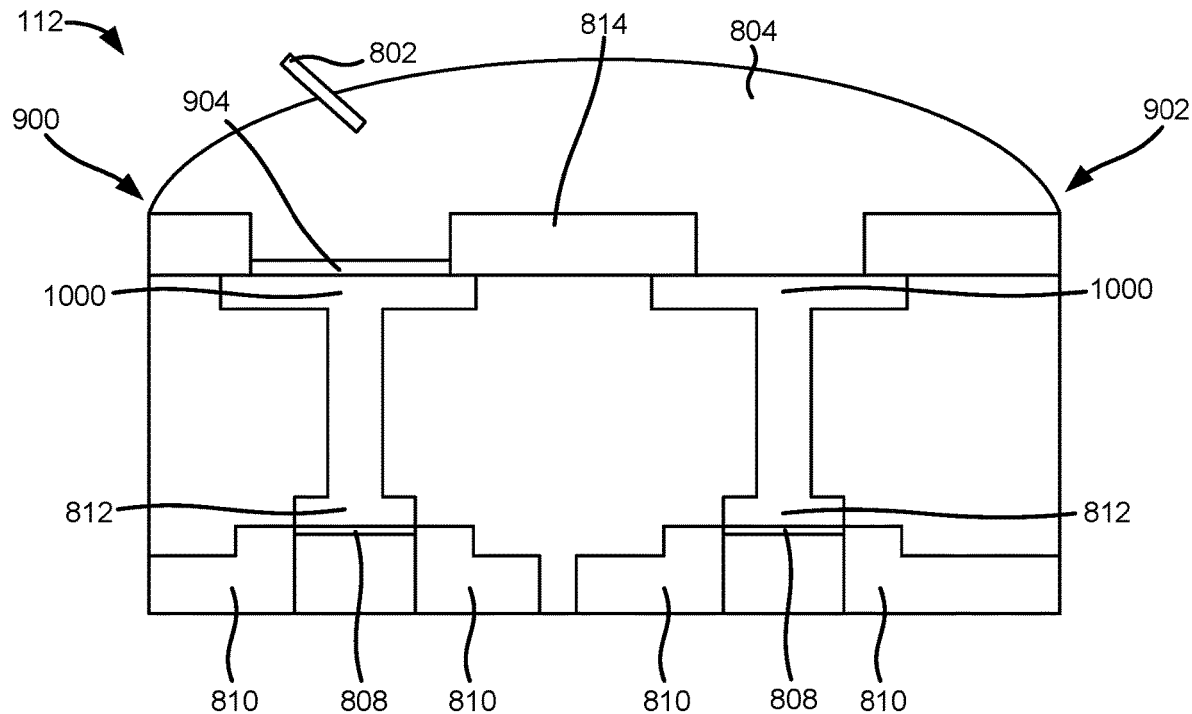
FIG. 10A illustrates a side view of another embodiment of a sensor of the system having extended gates and an external reference electrode.

FIG. 10A illustrates a side view of another embodiment of the sensor 112 having the active sensor 900 and the control sensor 902 each having an extended gate 1000.

Figure 10B:
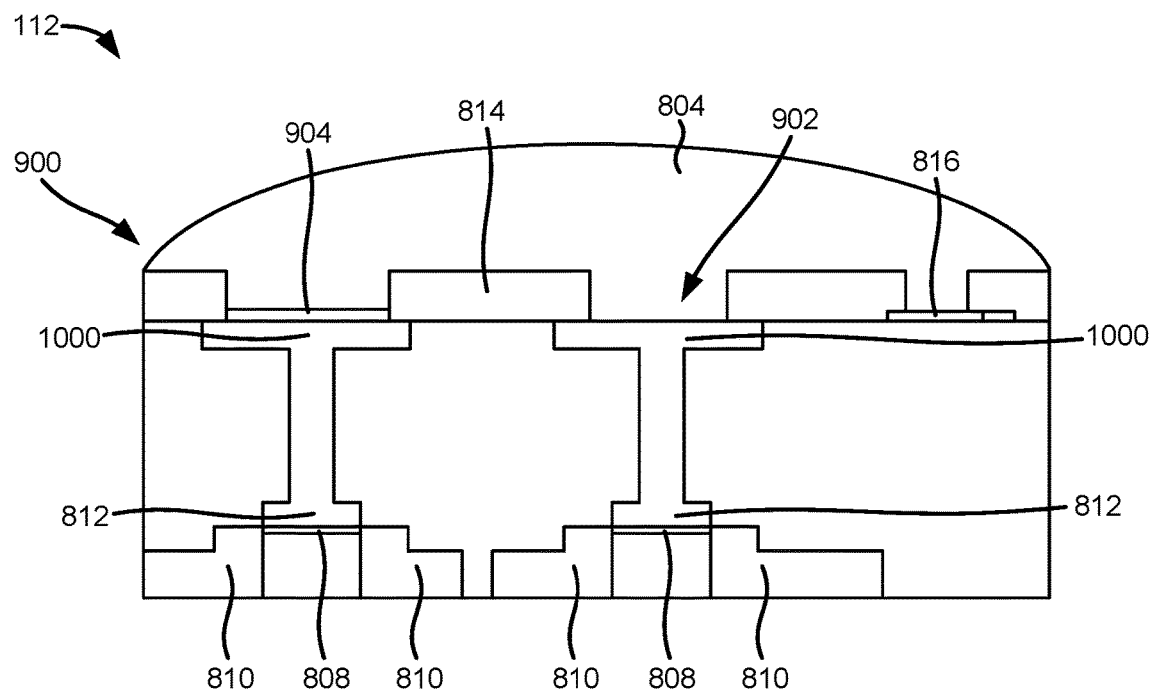
FIG. 10B illustrates a side view of another embodiment of a sensor of the system having extended gates and an on-chip reference electrode.

FIG. 10B illustrates a side view of another embodiment of the sensor 112 having the active sensor 900 and the control sensor 902 each having the extended gate 1000 and an on-chip electrode 816. As shown in FIGS. 10A and 10B, only the extended gate 1000 is exposed to the reaction mixture 804. The extended gate 1000 can interact with particles in the reaction mixture 804.

Figure 11:
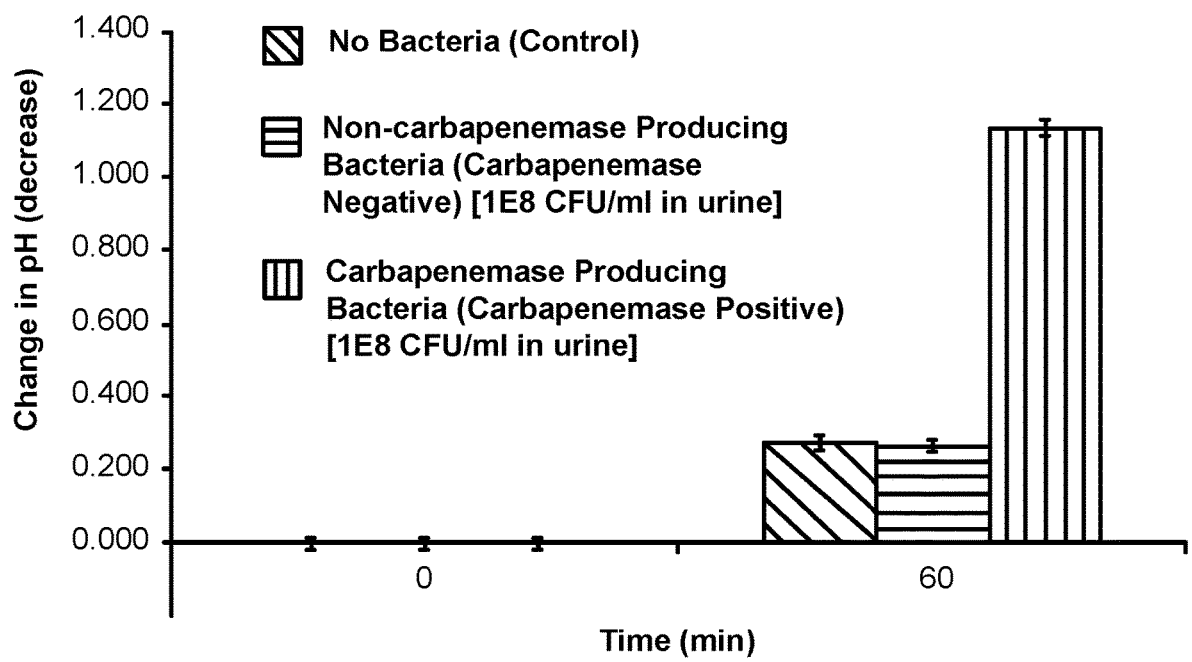
FIG. 11 illustrates a graph of the change in the pH of three samples monitored over time.

FIG. 11 is a bar graph illustrating the results of detection experiments conducted on three samples. In these experiments, urine samples comprising approximately $1*10^{\wedge}8$ CFU/mL carbapenemase producing bacteria were delivered or introduced to one set of filters 110 and urine samples comprising approximately $1*10^{\wedge}8$ CFU/mL non-carbapenemase producing bacteria were delivered or introduced to other filters 110. Control samples were also introduced to a third set of filters 110. All such filters 110 were washed with water and exposed or introduced to buffer solutions comprising a lysing agent 120 and at least one β-lactamase substrate 128 to form a series of reaction mixtures. In one embodiment, the lysing agent 120 can be a lysis reagent, such as ThermoFisher's B-PER™ Reagent, and the β-lactamase substrate 128 can be a β-lactam antibiotic such as ampicillin.

The reaction mixtures were then incubated for approximately 60 minutes at 37° C. and the pH of the reaction mixtures were measured using ion-sensitive field-effect transistor (ISFET) pH sensors representing the sensors 112. As shown in FIG. 11, the pH of the reaction mixtures containing the control sample and the non-carbapenemase producing bacteria showed little or no change while the pH of the reaction mixtures containing the carbapenemase producing bacteria showed a noticeable decrease (between −1.0 to −1.2) in their pH.

Figure 12:
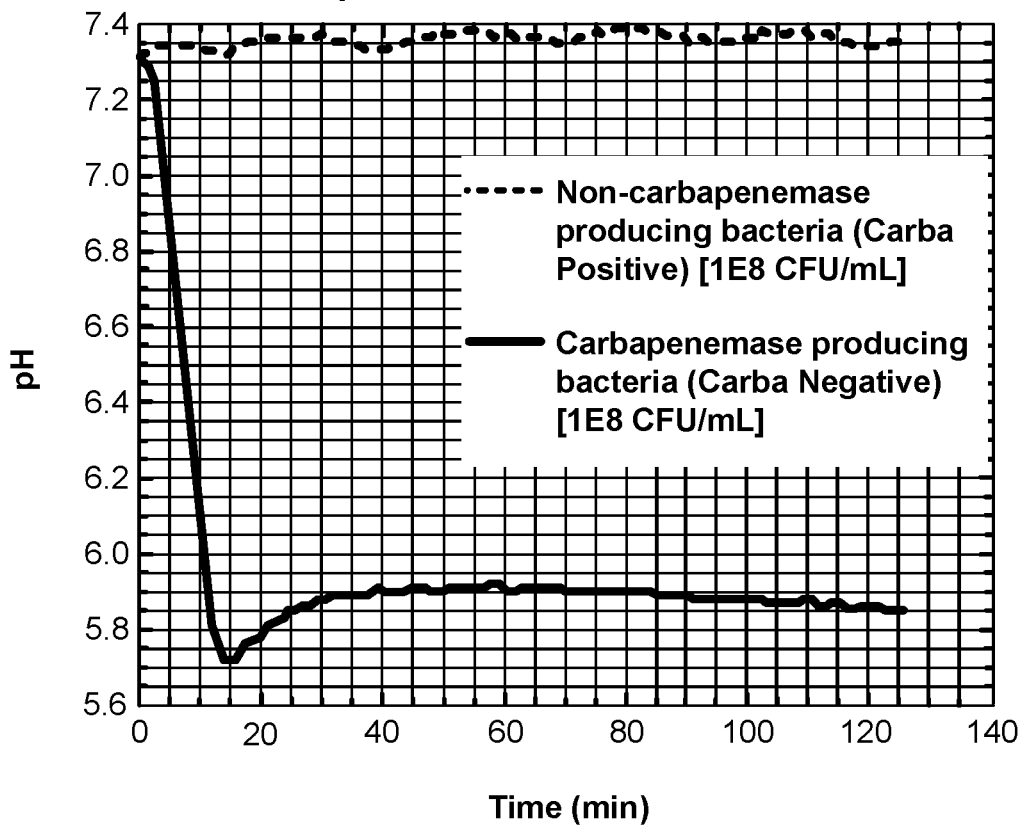
FIG. 12 illustrates a graph of the change in the pH of two samples monitored over time.

FIG. 12 shows line graphs illustrating real-time changes in the pH of two solutions. In these experiments, one urine sample comprising approximately $1*10^{\wedge}8$ CFU/mL carbapenemase producing bacteria was introduced to a buffer solution comprising a lysing agent 120 and β-lactamase activator 132 and another urine sample comprising approximately $1*10^{\wedge}8$ CFU/mL non-carbapenemase producing bacteria was introduced to a similar buffer solution. The lysing agent 120 included a lysis reagent, such as ThermoFisher's B-PER™ Reagent.

The resulting solutions were then incubated for approximately 60 minutes at 37° C. At least one β-lactamase substrate 128 was added to each solution and the pH of each solution was measured in real-time. The β-lactamase substrate 128 can be a β-lactam antibiotic such as imipenem. The pH of each solution was measured using ISFET pH sensors 112 in real time. As shown in FIG. 12, the pH of the solution containing the non-carbapenemase producing bacteria showed little or no change while the pH of the solution containing the carbapenemase producing bacteria showed a noticeable decrease in its pH (from approximately pH 7.4 to pH 5.7).

Figure 13:
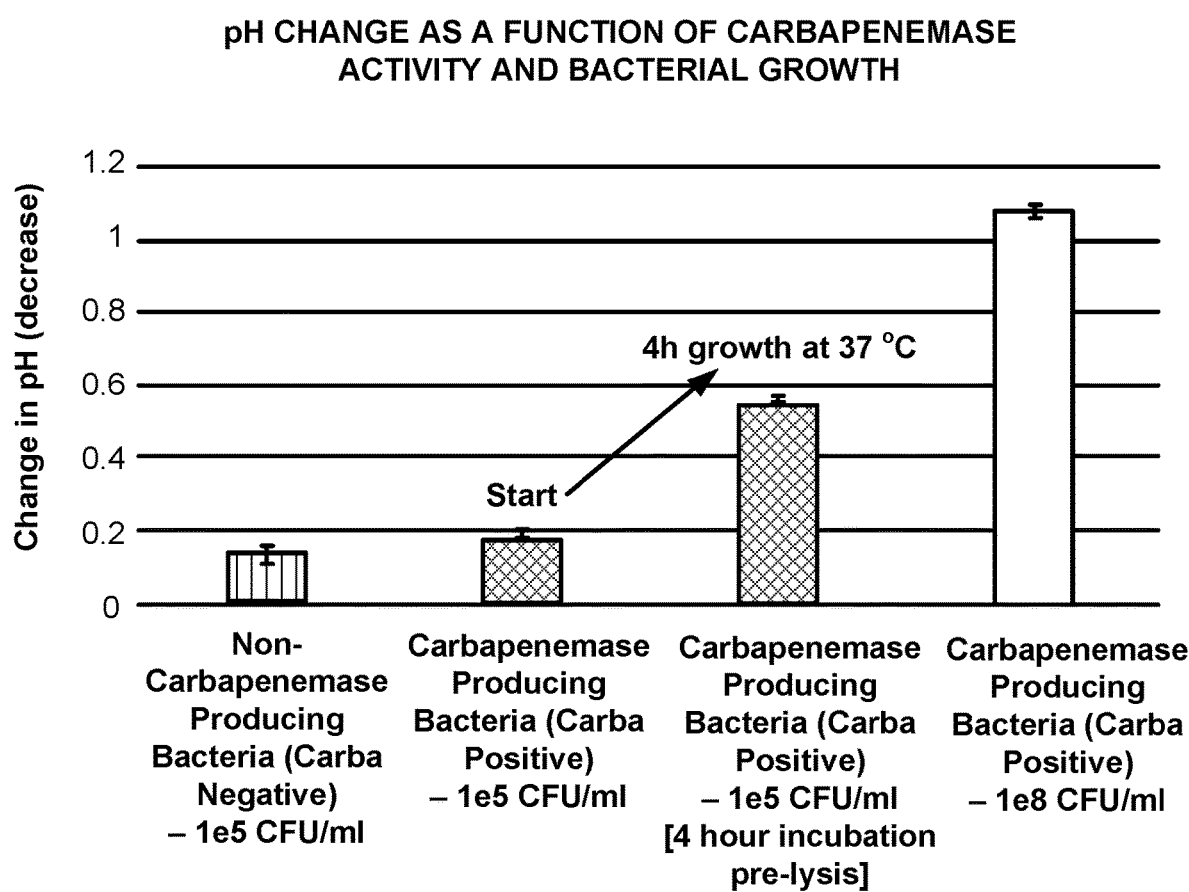
FIG. 13 illustrates a graph of pH change as a function of carbapenemase activity and bacterial growth for four hours at 37° C.

FIG. 13 is a bar graph illustrating the results of detection experiments aimed at increasing the limit of detection of the procedures described herein. In these experiments, urine samples comprising approximately $1*10^{\wedge}5$ CFU/mL non-carbapenemase producing bacteria were delivered or introduced to a first set of filters 110 and urine samples comprising approximately $1*10^{\wedge}5$ CFU/mL carbapenemase producing bacteria were delivered or introduced to a second set of filters 110. In addition, urines samples comprising approximately $1*10^{\wedge}8$ CFU/mL carbapenemase producing bacteria were delivered or introduced to a third set of filters 110 to act as a positive control.

All such filters 110 were then washed with water and some of the filters 110 exposed to the approximately $1*10^{\wedge}5$ CFU/mL carbapenemase producing bacteria were then allowed to incubate on the filters 110 at 37° C. for up to four hours prior to exposing the filters 110 to the lysing agent 120. These filters 110, along with the non-incubated filters 110, were then exposed or introduced to buffer solutions comprising a lysing agent 120 and at least one β-lactamase substrate 128 to form a series of reaction mixtures. In one embodiment, the lysing agent 120 can be a lysis reagent, such as ThermoFisher's B-PER™ Reagent, and the β-lactamase substrate 128 can be a β-lactam antibiotic such as ampicillin.

The reaction mixtures were then incubated for approximately 60 minutes at 37° C. and the pH of the reaction mixtures were measured using ISFET pH sensors 112. As shown in FIG. 13, the pH of the reaction mixtures containing non-carbapenemase producing bacteria showed little or no change. Moreover, the pH of the reaction mixtures containing carbapenemase producing bacteria which had not been incubated on the filters 110 prior to the lysing step also showed little or no change. However, the pH of the reaction mixtures containing carbapenemase producing bacteria which had been incubated on the filters 110 for up to four hours prior to the lysing step showed a noticeable decrease (Δ pH 0.6) in their solution pH. Moreover, the pH of the reaction mixtures containing the positive control of $1*10^{\wedge}8$ CFU/mL of carbapenemase producing bacteria showed an even more noticeable pH decrease (approximately Δ pH 1.1). FIG. 13 is significant for showing that the limits of detection for the methods and systems described herein can be increased by incubating the bacteria 102 or sample 104 on the filter 110 or filter surface 118 for a period of time prior to introducing the lysing agent 120 to the bacteria 102.

Figure 14:
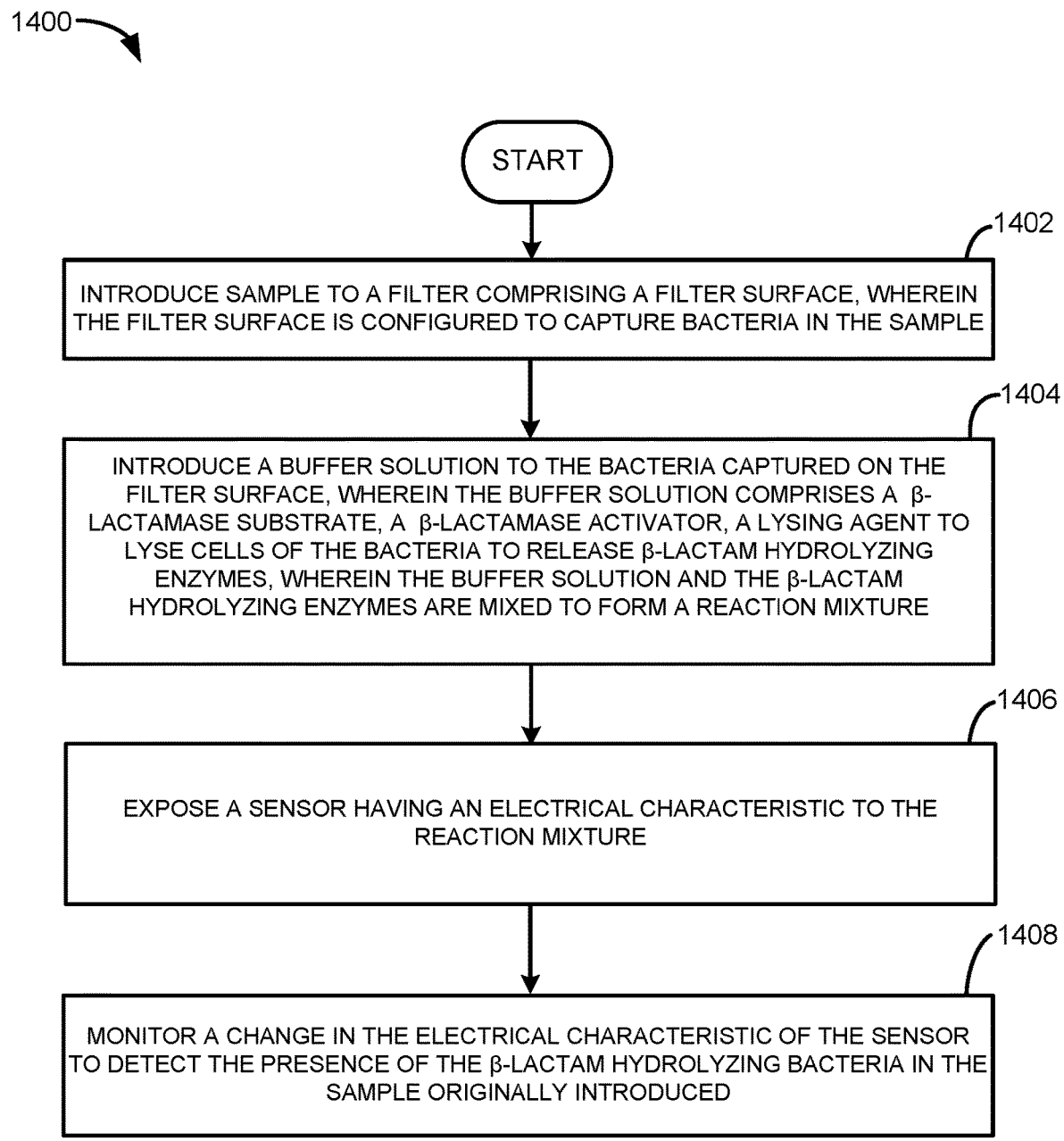
FIG. 14 illustrates one embodiment of a method for detecting β-lactam antibiotic hydrolyzing bacteria in a sample.

FIG. 14 illustrates a method 1400 of detecting the presence of β-lactam antibiotic hydrolyzing bacteria 136 in a sample 104. The method 1400 can include introducing the sample 104 to a filter 110 comprising a filter surface 118 in step 1402. The filter surface 118 can be configured to capture bacteria 102 in the sample 104. The method 1400 can also include introducing a buffer solution 124 to the bacteria 102 captured on the filter surface 118 in step 1404. The buffer solution 124 can comprise a β-lactamase substrate 128, a β-lactamase activator 132, and a lysing agent 120 to lyse cells of the bacteria 102 to release β-lactam antibiotic hydrolyzing enzymes 122. The buffer solution 124 and the β-lactam antibiotic hydrolyzing enzymes 122 can be mixed to form a reaction mixture 126. The method 1400 can also include exposing a sensor 112 having an electrical characteristic to the reaction mixture 126 in step 1406 and monitoring a change in the electrical characteristic of the sensor 112 to detect the presence of the β-lactam antibiotic hydrolyzing bacteria 136 in the sample 104 originally introduced in step 1408

Figure 15:
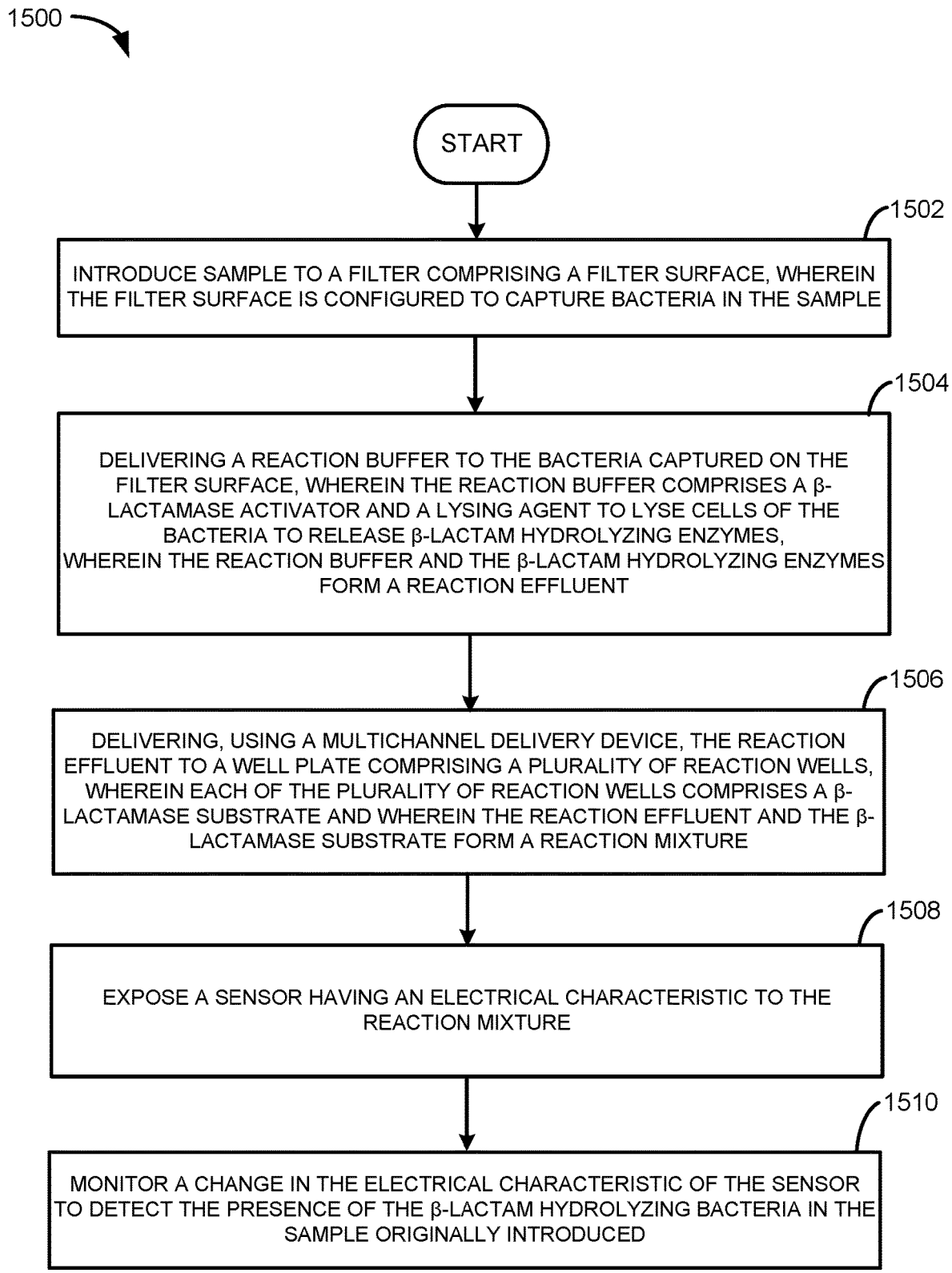
FIG. 15 illustrates another embodiment of a method for detecting β-lactam antibiotic hydrolyzing bacteria in a sample.

FIG. 15 illustrates another method 1500 of detecting the presence of β-lactam antibiotic hydrolyzing bacteria 136 in a sample 104. The method 1500 can include introducing the sample 104 to a filter 110 comprising a filter surface 118 in step 1502. The filter surface 118 can be configured to capture bacteria 102 in the sample 104. The method 1500 can also include delivering a reaction buffer 201 to the bacteria captured on the filter surface 118, wherein the reaction buffer 201 comprises a β-lactamase activator 132, and a lysing agent 120 to lyse cells of the bacteria to release β-lactam antibiotic hydrolyzing enzymes 122 in step 1504. The reaction buffer 201 and the β-lactam antibiotic hydrolyzing enzymes 122 mix to form a reaction effluent 203.

The method 1500 can also include delivering, using a multichannel delivery device 206, the reaction effluent 203 to a well plate 202 comprising a plurality of reaction wells 204, wherein each of the plurality of reaction wells 204 comprises a β-lactamase substrate 128, and wherein the reaction effluent 203 and the β-lactamase substrate 128 form a reaction mixture 212 in step 1506. The method 1500 can also include exposing a pH sensor 112 to the reaction mixture 212 in step 1508 and monitoring the pH of the reaction mixture 212 to detect the presence of the β-lactam antibiotic hydrolyzing bacteria 136 in the sample 104 originally introduced in step 1510.

The flowcharts or process flows depicted in FIGS. 14-15 do not require the particular order shown to achieve the desired result and certain steps or processes may occur in parallel.

Each of the individual variations or embodiments described and illustrated herein has discrete components and features which may be readily separated from or combined with the features of any of the other variations or embodiments. Modifications may be made to adapt a particular situation, material, composition of matter, process, process act(s) or step(s) to the objective(s), spirit or scope of the present invention.

Methods recited herein may be carried out in any order of the recited events that is logically possible, as well as the recited order of events. For example, the flowcharts or process flows depicted in the figures do not require the particular order shown to achieve the desired result. Moreover, additional steps or operations may be provided or steps or operations may be eliminated to achieve the desired result.

It will be understood by one of ordinary skill in the art that all or a portion of the methods disclosed herein may be embodied in a non-transitory machine readable or accessible medium comprising instructions readable or executable by a processor or processing unit of a computing device or other type of machine.

Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations or embodiments described herein. Further, the scope of the disclosure fully encompasses other variations or embodiments that may become obvious to those skilled in the art in view of this disclosure. The scope of the present invention is limited only by the appended claims.

What is claimed is:

1. A method of detecting the presence of β-lactam antibiotic hydrolyzing bacteria in a sample, the method comprising:
introducing the sample comprising the β-lactam antibiotic hydrolyzing bacteria to a container housing a filter, wherein the filter comprises a filter surface, wherein the filter surface is a mesh or matrix structure made of a polymeric material, wherein the filter is secured by the container housing;
introducing a buffer solution to the β-lactam antibiotic hydrolyzing bacteria, wherein the buffer solution comprises a β-lactamase substrate, a β-lactamase activator, and a lysing agent to lyse cells of the bacteria to release-lactam antibiotic hydrolyzing enzymes,
wherein the buffer solution and the B-lactam antibiotic hydrolyzing enzymes form a reaction mixture;
exposing a sensor having an electrical characteristic to the reaction mixture, wherein the sensor comprises an active electrode and a quasi-reference electrode, wherein the active electrode and the quasi-reference electrode are disposed on a base dielectric layer; and
monitoring a change in the electrical characteristic of the sensor to detect the presence of the β-lactam antibiotic hydrolyzing bacteria in the sample originally introduced, wherein the change in the electrical characteristic is a change in a voltage potential between the active electrode and the quasi-reference electrode measured by a parameter analyzer coupled to the active electrode and the quasi-reference electrode.

2. The method of claim 1, wherein the change in the electrical characteristic of the sensor is a result of a change in a solution characteristic of the reaction mixture.

3. The method of claim 2, wherein the change in the solution characteristic is a pH change.

4. The method of claim 1, wherein the β-lactamase substrate comprises at least one of carbapenems, cephamycins, penicillins, cephalosporins, and monobactams.

5. The method of claim 1, wherein the β-lactam antibiotic hydrolyzing enzymes comprise at least one of extended spectrum β-lactamases, inhibitor-resistant β-lactamases, AmpC-type B-lactamases, and carbapenemases.

6. The method of claim 1, wherein the B-lactamase activator includes at least one of a divalent cation, a divalent cation salt, or a combination thereof.

7. The method of claim 1, further comprising introducing a β-lactamase inhibitor to the reaction mixture.

8. The method of claim 1, further comprising maintaining a reaction temperature of between 20° C. and 40° C. upon introduction of the buffer solution.

9. The method of claim 1, wherein monitoring the change in the electrical characteristic of the sensor involves monitoring the change in the electrical characteristic between 1 minute and 120 minutes in order to detect the presence of the β-lactam antibiotic hydrolyzing bacteria in the sample originally introduced.

10. The method of claim 1, wherein the quasi-reference electrode is made in part of a metallic material.

11. The method of claim 1, wherein the filter comprises filter pores extending through the filter.

12. The method of claim 1, further comprising incubating the β-lactam antibiotic hydrolyzing bacteria in the sample within the container at an incubation temperature between 20° C. and 40° C.

13. The method of claim 2, wherein the change in the solution characteristic is a result of ions or organic molecules produced by, consumed by, or otherwise attributed to the reaction between the β-lactam antibiotic hydrolyzing enzymes and the β-lactamase substrate.

\* \* \* \* \*